(12) United States Patent
Ookawa

(10) Patent No.: US 8,983,030 B2
(45) Date of Patent: Mar. 17, 2015

(54) INSPECTION MACHINE FOR PRINTED CIRCUIT BOARD

(71) Applicant: Yamaha Hatsudoki Kabushiki Kaisha, Shizuoka-ken (JP)

(72) Inventor: Naonobu Ookawa, Shizuoka (JP)

(73) Assignee: Yamaha Hatsudoki Kabushiki Kaisha, Shizuoka (JP)

( * ) Notice: Subject to any disclaimer, the term of this patent is extended or adjusted under 35 U.S.C. 154(b) by 159 days.

(21) Appl. No.: 13/853,851

(22) Filed: Mar. 29, 2013

(65) Prior Publication Data

US 2013/0279655 A1 Oct. 24, 2013

(30) Foreign Application Priority Data

Apr. 20, 2012 (JP) ................................. 2012-096814

(51) Int. Cl.
*G01N 23/04* (2006.01)
*H05K 13/08* (2006.01)

(52) U.S. Cl.
CPC ................ *G01N 23/04* (2013.01); *H05K 13/08* (2013.01)
USPC .......................................................... 378/62

(58) Field of Classification Search
USPC ........................................... 378/19, 62, 98.8
See application file for complete search history.

(56) References Cited

U.S. PATENT DOCUMENTS

| 6,823,044 B2* | 11/2004 | Rosner ........................ 378/98.8 |
| 2001/0030298 A1 | 10/2001 | Sakaguchi |
| 2011/0249795 A1* | 10/2011 | Sugita et al. .................... 378/62 |

FOREIGN PATENT DOCUMENTS

| JP | 02-052246 A | 2/1990 |
| JP | H06-331571 A | 12/1994 |
| KR | 10-0730830 B1 | 6/2007 |

OTHER PUBLICATIONS

An Office Action issued by the Korean Patent Office on Jun. 9, 2014, which corresponds to Korean Patent Application No. 10-2013-0042898 and is related to U.S. Appl. No. 13/853,851; with English language summary.

* cited by examiner

*Primary Examiner* — Irakli Kiknadze
(74) *Attorney, Agent, or Firm* — Studebaker & Brackett PC

(57) ABSTRACT

Disclosed is an inspection machine provided with an imaging device that capture a close-up image of the imaging target portion of the printed circuit board on which a plurality of electronic components are mounted, by coming close to a printed circuit board. The inspection machine has a sensor unit that detects the heights of the electronic components on the printed circuit board by irradiation light in a first direction that is along the surface of the printed circuit board. Control means of the inspection machine sets a limit distance to a position above the highest electronic component among heights detected from the electronic components. The control means also restricts a facing distance by which the imaging device is accepted to approach the printed circuit board, to be the limit distance.

9 Claims, 22 Drawing Sheets

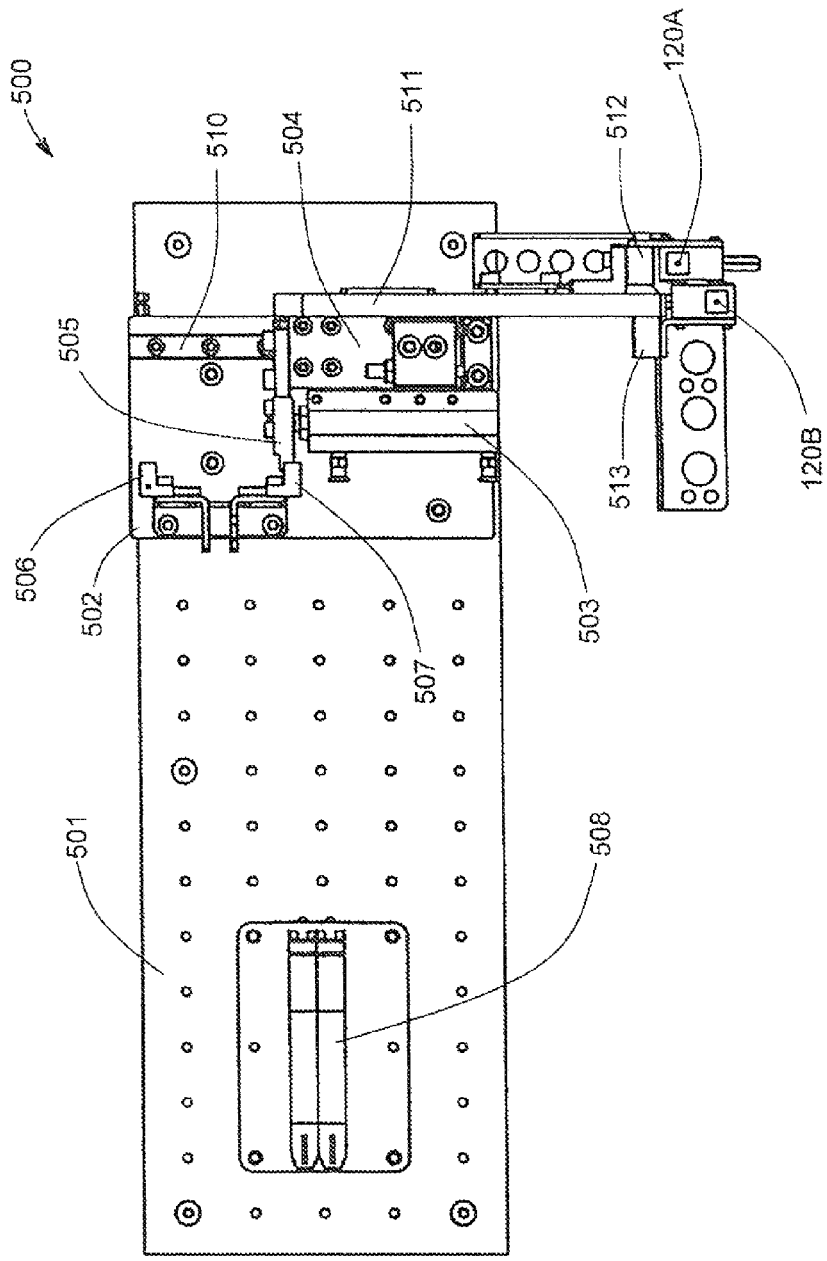

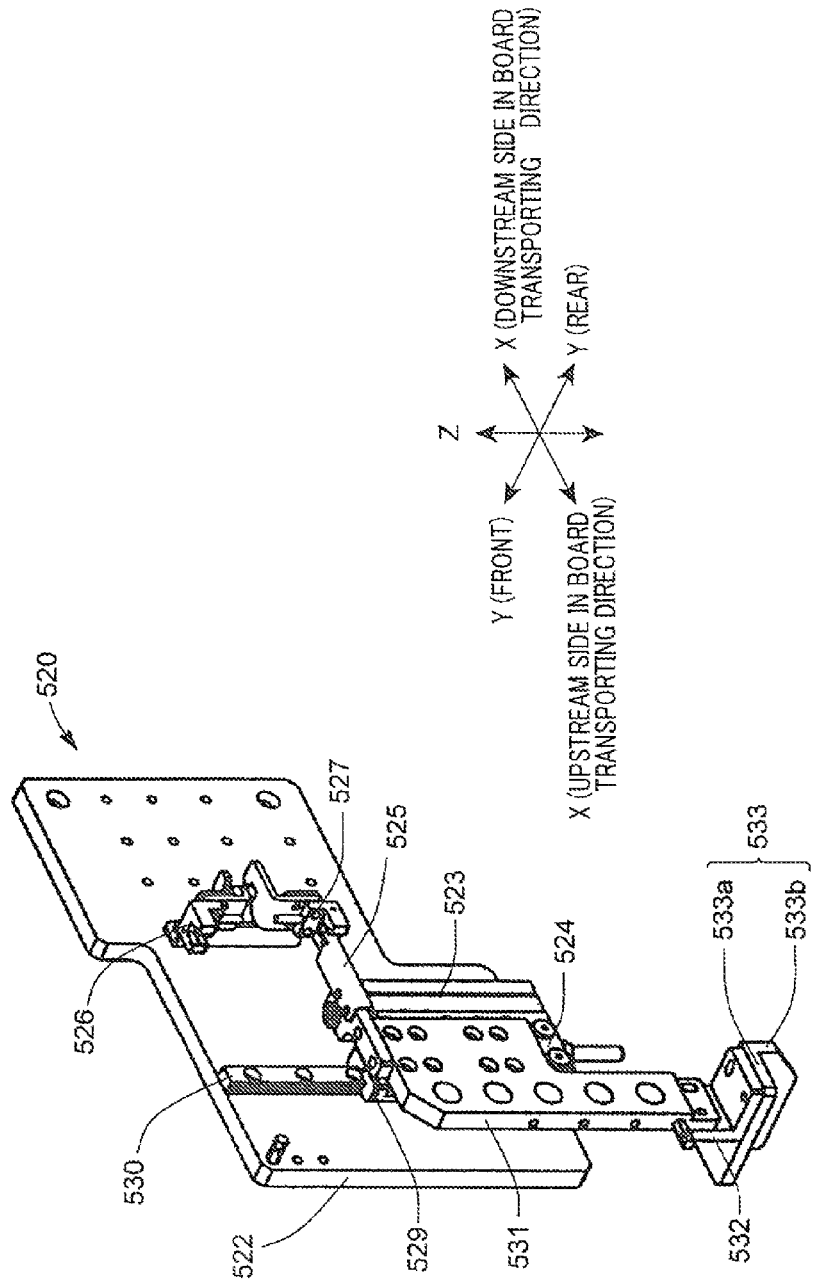

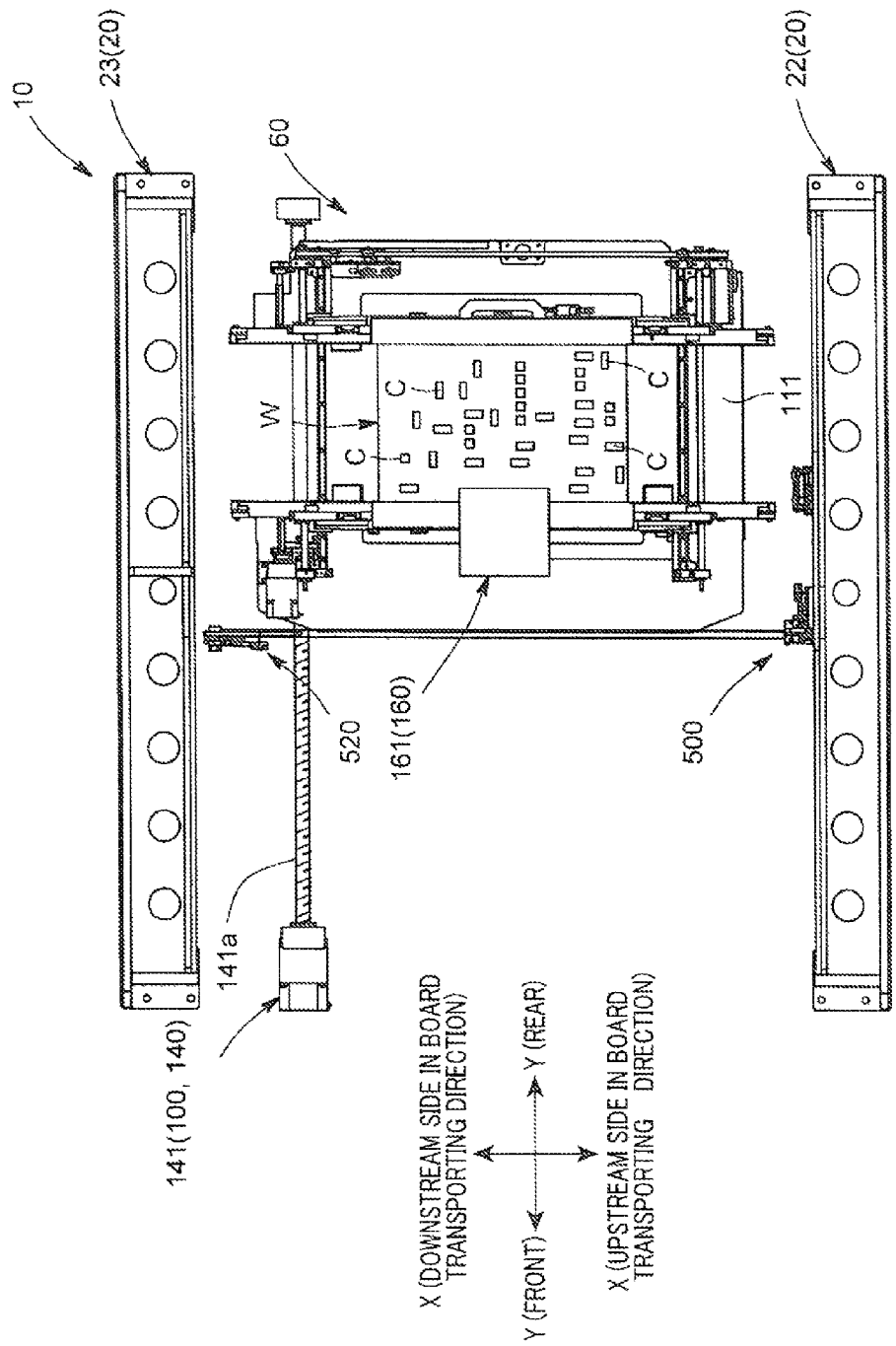

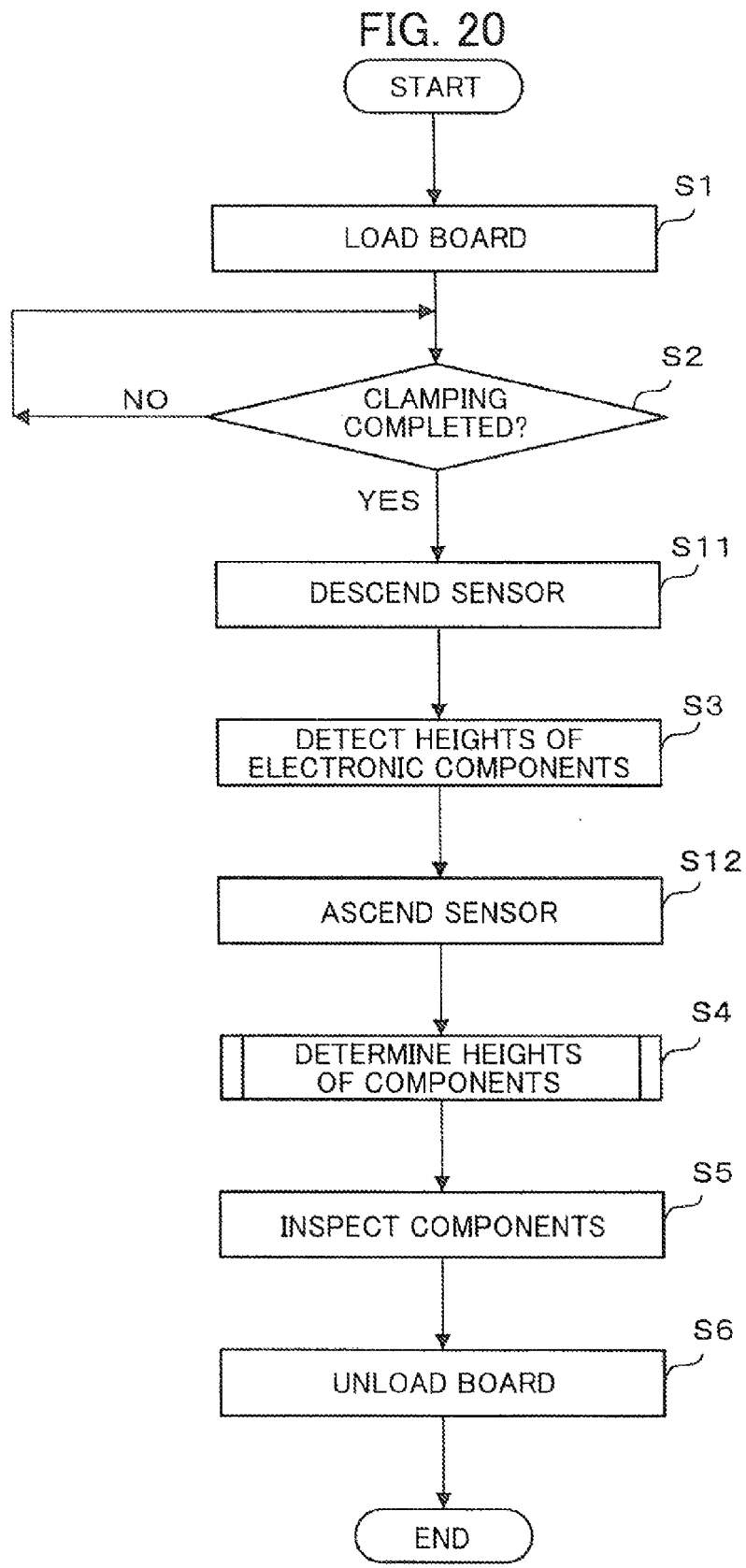

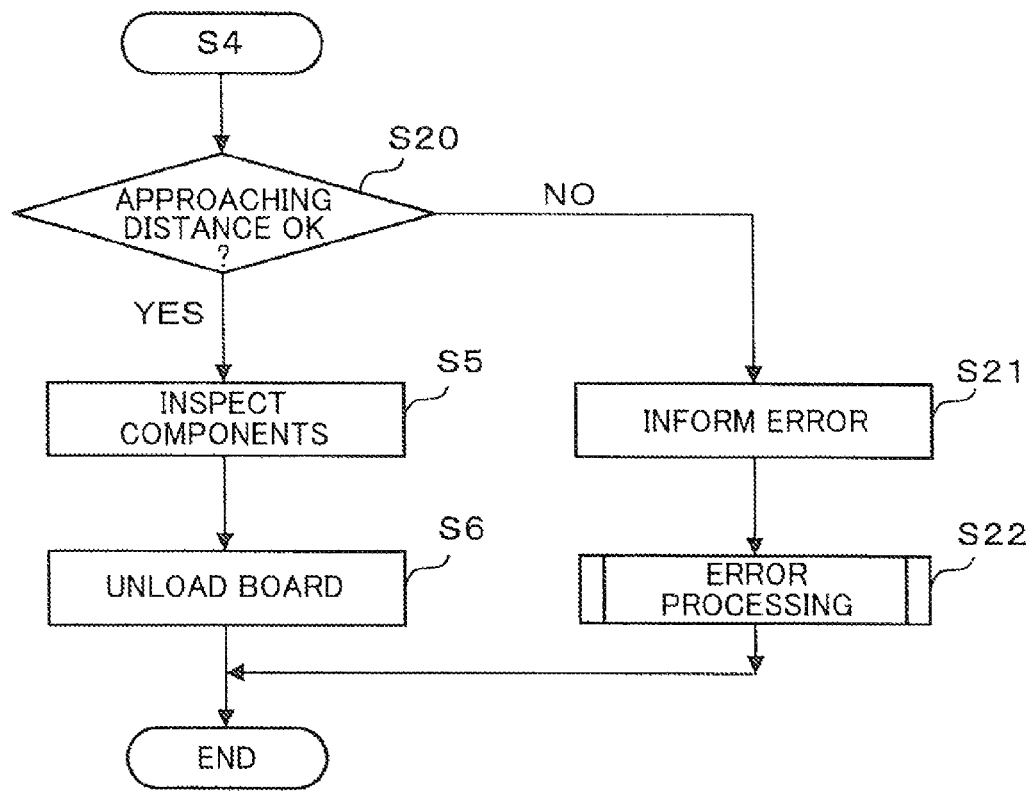

INSPECTION MACHINE FOR PRINTED CIRCUIT BOARD

BACKGROUND OF THE INVENTION

1. Field of the Invention

The present invention relates to an inspection machine for a printed circuit board, and more particularly to an inspection machine for a printed circuit board including an imaging device having a function (or close-up function) to capture a high resolution image by coming close to the printed circuit board.

2. Description of the Background Art

For example, an inspection machine disclosed in Japanese Patent Application Laid-Open No. H02-52246 has an imaging device in the form of an X-ray irradiation unit and an X-ray camera which face each other with respect to a printed circuit board therebetween.

The X-ray irradiation unit irradiates an X-ray onto the printed circuit board. The X-ray camera receives the X-ray transmitted through the printed circuit board, and captures an image of an inspection target portion of the printed circuit board. Here the resolution of the image captured by the X-ray camera depends on the ratio of a distance from a light source of the X-ray irradiation unit to the printed circuit board (hereafter called "irradiation distance"), and a distance from the printed circuit board to the X-ray camera (hereafter called "transmission distance"). If the so-called close-up function is needed, the X-ray irradiation unit approaches the printed circuit board so that the irradiation distance becomes relatively shorter than the transmission distance.

Recently a close-up function with high resolution is demanded. To meet this demand, it is necessary to move the X-ray irradiation unit close to the printed circuit board so as to minimize the irradiation distance. Therefore, the electronic components mounted on the printed circuit board and the X-ray irradiation unit tends to easily interfere with each other when close-up imaging, that requires high resolution, is performed. A possible method to prevent this interference is measuring the height of each electronic component from a point above the printed circuit board using a distance detection means which measures the distance between the printed circuit board and the X-ray irradiation unit. However, many electronic components are usually dispersed on the printed circuit board. This means that measurement is required for so many measurement points, and therefore measuring the height of each electronic component from a point above the printed circuit board is not practical.

Another possible method is registering data in a server for each printed circuit board to be manufactured, supplying the registered data to an inspection machine and restricting the height to approach each printed circuit board (or each item number). In this case, however, it is possible that the data and actual product may mismatch due to incidents such as data input error, communication error, change of transporting sequence, and due to the state of components mounted irregularly (e.g. part of the components is delicately-mounted on the same point). In other words, data management alone is insufficient solve interference.

SUMMARY OF THE INVENTION

With the foregoing in view, it is an object of the present invention to provide an inspection machine for a printed circuit board having an imaging device having a close-up function to image the printed circuit board at a close distance, wherein interference between the imaging device and the printed circuit board is surely prevented.

To solve the above problem, the present invention provides an inspection machine for a printed circuit board on which a plurality of electronic components is mounted. The inspection machine is provided with: an imaging device having a function for capturing a close-up of a inspection target portion of the printed circuit board by approaching the printed circuit board; detection unit for detecting heights of electronic components on the printed circuit board to be subjected to inspections by irradiation light that is irradiated onto the printed circuit board in a first direction that is along a surface of the printed circuit board; displacement unit for relatively displacing the detection unit and the printed circuit board along the surface of the printed circuit board in a second direction that crosses the first direction; and control unit that controls the detection unit and the displacement unit. The control unit controls the detection unit to detect the heights of the electronic components mounted on the printed circuit board, by activating the detection unit and the displacement unit before capturing the printed circuit board by the imaging device. The control unit sets a limit distance to a position higher than the highest electronic component among heights detected from the electronic components. The control unit thereby restricts the facing distance, by which the imaging device is accepted to approach the printed circuit board, to be the limit distance. According to this aspect, the heights of the electronic components mounted on the printed circuit board are detected before imaging is executed by the imaging device. In order to prevent interference with the electronic components, the height, by which the imaging device is able to approach the printed circuit board, is restricted to the height corresponding to the highest electronic component among heights detected from the electronic components. Thus the interference between the imaging device and the electronic components mounted on the printed circuit board can be completed prevented. To detect the heights of the electronic components here, the irradiation light of the detection unit is irradiated in the first direction along the surface of the printed circuit board. At the same time, the detection unit and the printed circuit board are relatively moved in the second direction which crosses the first direction by the displacement unit. Due to the relative movement of the detection unit and the printed circuit board, the entire surface of the printed circuit board is scanned, and the heights of all the electronic components mounted on the printed circuit board can be detected in an exhaustive manner.

These and other objects, features and advantages of the invention will become more apparent upon reading the following detailed description along with the accompanying drawings.

BRIEF DESCRIPTION OF THE DRAWINGS

FIG. 16 is a schematic front view of the sensor unit;

FIG. 17A is a perspective view depicting an appearance of a mirror unit according to second embodiment;

FIG. 18 is a schematic plan view depicting the inspection machine of second embodiment, where a part of the inspection machine is omitted;

FIG. 20 is a flow chart depicting an operation of the inspection machine according to second embodiment; and FIG. 21 is a flow chart depicting a part of the operation of the inspection machine according to third embodiment.

DESCRIPTION OF THE PREFERRED EMBODIMENTS

Preferred embodiments of the present invention will now be described with reference to the accompanying drawings.

In the following description, each portion of an inspection machine 10 according to an embodiment of the present invention is described. The description will follow a rectangular coordinate system where an X axis is a direction where the printed circuit board to be subjected to inspections W is transported, a Y axis is a horizontal direction that is perpendicular to the X axis, and a Z axis is a vertical direction. Many electronic components C are mounted on the printed circuit board W, of which conductive portions are soldered. The inspection machine 10 according to this embodiment is an apparatus configured such that each soldered portion of each electronic component C is mainly inspected, and the acceptability of each printed circuit board W is inspected.

Figure 1:
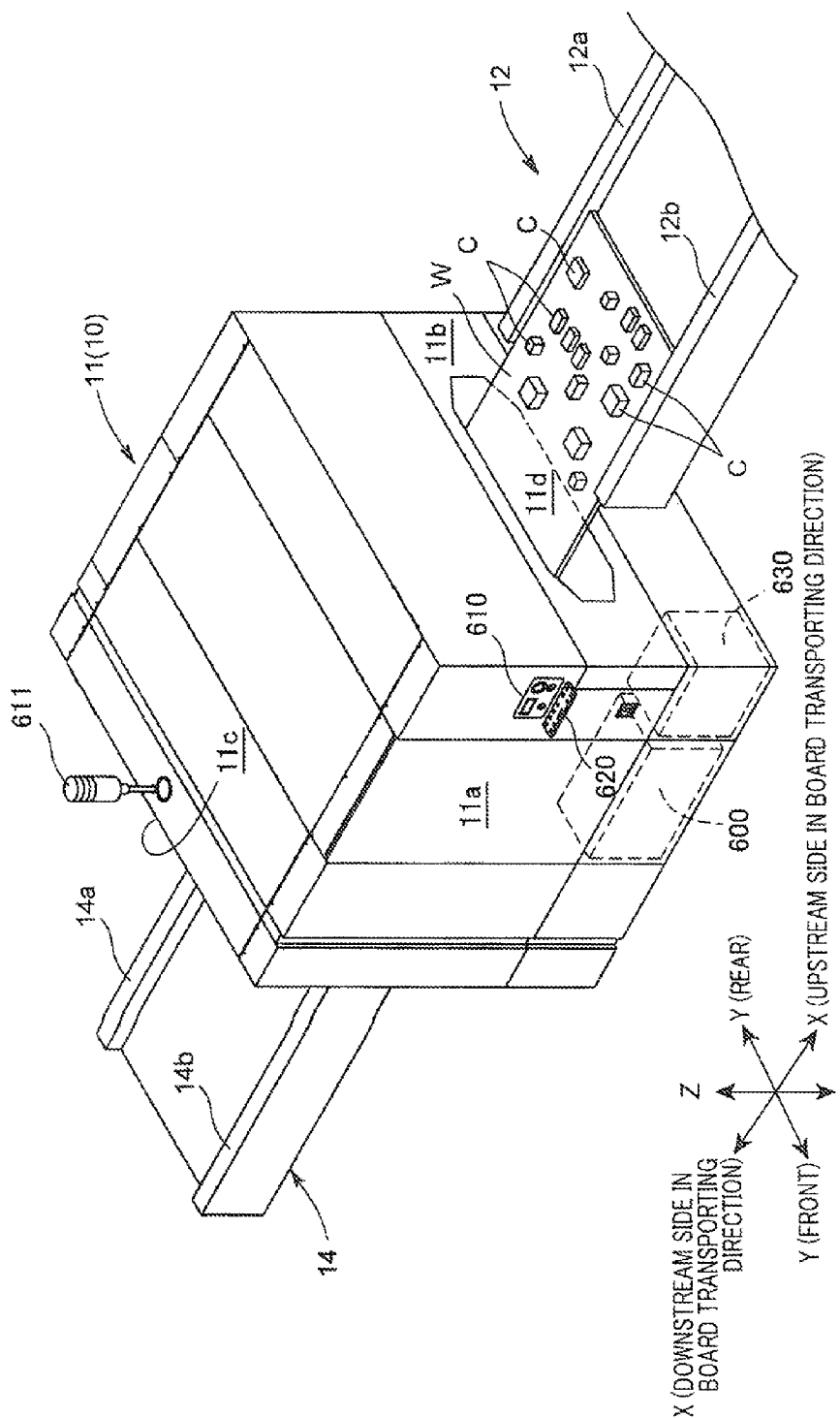
FIG. 1 is a perspective view depicting an appearance of an inspection machine according to first embodiment, which is an embodiment of the present invention.

As shown in FIG. 1, the inspection machine 10 has a housing 11 shielded by lead or the like. The housing 11 is an approximate cube, and the front face 11a thereof faces one side in the Y axis direction. A pair of board conveyors 12 and 14 for loading or unloading a board W is installed on both sides of the housing 11. Each of the board conveyors 12 and 14 is formed by a belt conveyor pair 12a and 12b or 14a and 14b respectively. According to the specification of the equipment to be installed, one of the board conveyors 12 and 14 will be a board loading conveyor and the other will be a board unloading conveyor. In the facility where the inspection machine 10 is installed, a printed circuit board W loaded by the board loading conveyor is inspected in the housing 11. Then, the inspected board w will be unloaded from the inspection machine 10 by the board unloading conveyor. In the example in FIG. 1, the board conveyor 12 at the right is the loading conveyor, and the board conveyor 14 at the left is the unloading conveyor. A pair of openings 11d and 11e for loading or unloading a printed circuit board W are opened (see FIG. 2) in the walls 11b and 11c of the housing 11, facing the board conveyors 12 and 14, respectively. A shutter mechanism is installed in each of the openings 11d and 11e. The shutter mechanism normally closes each of the openings 11d and 11e, so as to prevent a radiation leak. When a printed circuit board W is loaded or unloaded, each shutter mechanism opens the opening 11d and 11e so that the printed circuit board W can be loaded or unloaded. In this embodiment, a control unit 600, for controlling the all devices, is installed in the housing 11. A display panel 610 and a keyboard 620 connected with the control unit 600 are installed on the front face of the housing 11. A lamp 611 to indicate the operation state is vertically set on the top of the housing 11. A power supply unit 630 is installed at the upstream side of the control unit 600 in the board traveling direction.

Figure 2:
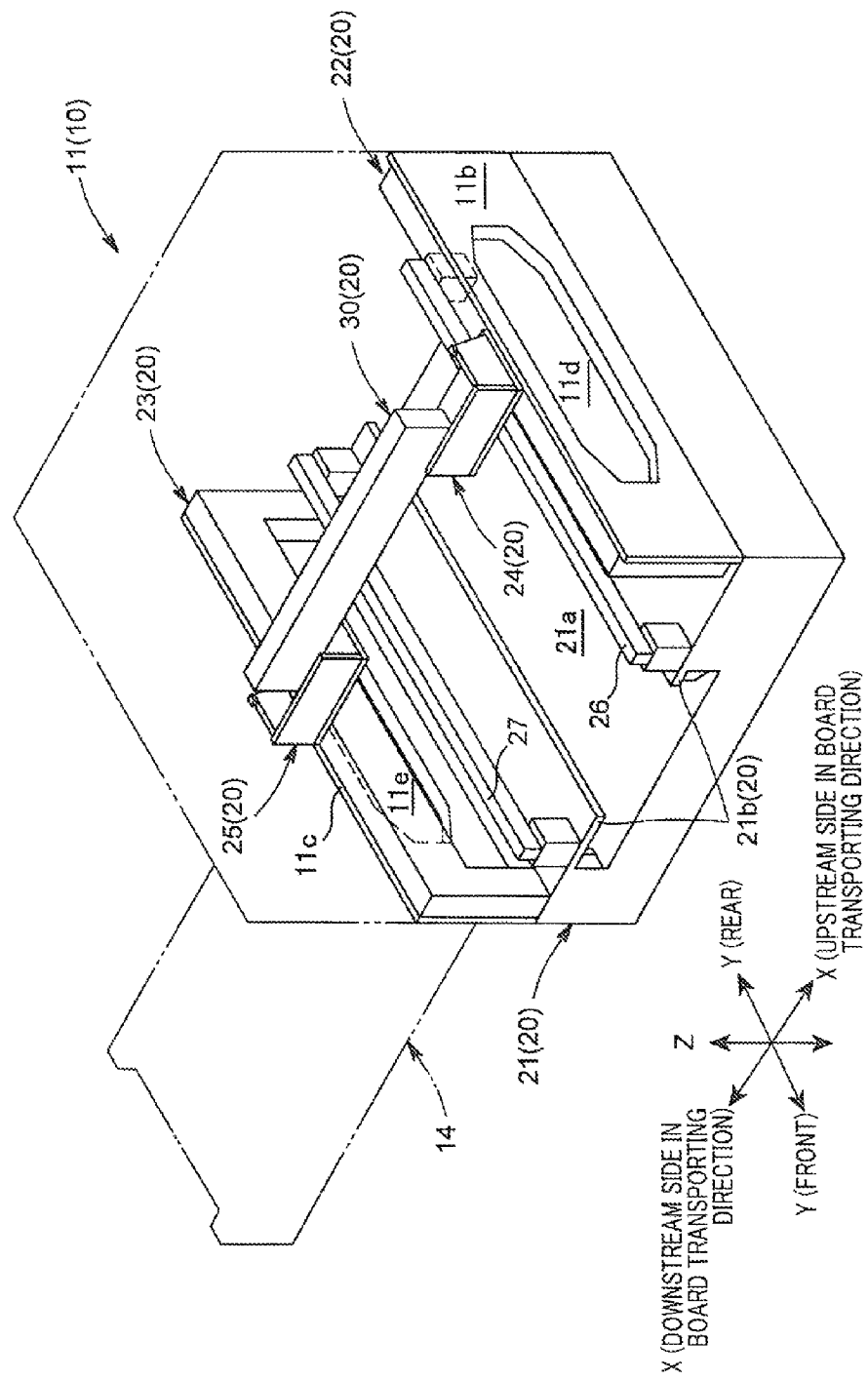
FIG. 2 is a perspective view depicting a structure of the inspection machine according to first embodiment.

As shown in FIG. 2, a structure 20 to support each unit installed in the inspection machine 10 is disposed in the housing 11. The structure 20 includes a base 21 forming a bottom portion of the housing 11, a pair of gate portions 22 and 23 which are vertically set on the base 21 as a pair in order to reinforce the inner wall portions on one end and the other end in the X axis direction, a pair of frame portions 24 and 25 each of which is secured at the center on each gate portion 22 or 23, and a beam 30 crossing between the frame portions 24 and 25. Each of these elements of the structure 20 is in the form of a combination of various steel materials and sheet metal members.

The base 21 has a bottom portion 21a where a center part in the X axis direction is recessed with a rectangular shape, and extends in the Y axis direction. A later mentioned X-ray camera unit 40 is disposed in the bottom portion 21a (see FIG. 3). A shelf portion 21b is integrated on both sides of the bottom portion 21a of the base 21, extending horizontally along the Y axis direction, where a part of the shelf portion 21b protrudes toward the center along the X axis direction. A Y axis rail 26 or 27 that faces the gate portion 22 or 23 is formed respectively on the top face of each shelf portion 21b. Each rail 26 or 27 is for moving the board table 60 in the front and back directions along the Y axis direction via a movable frame 111 of a table driving mechanism 100, which will be described later.

Each of the gate portions 22 and 23 is formed in a gate configuration that crosses over the corresponding opening 11d or 11e of the housing 11, and encloses a shutter mechanism installed on the corresponding wall 11b or 11c of the housing 11, respectively.

In each of the frame portions 24 or 25, the bottom portion is welded to the top portion of the corresponding gate portion 22 or 23, and the top face thereof is welded to each end of the beam 30 in the X axis direction, respectively. The frame portions 24 and 25, along with the gate portions 22, 23 and the beam 30, configure a firm frame structure.

The beam 30 is a structure to support the X-ray irradiation unit 160, which will be described in detail later. The X-ray irradiation unit 160 and the X-ray camera unit 40, which is described next, are examples of units constituting the imaging device of the present invention.

Figure 3:
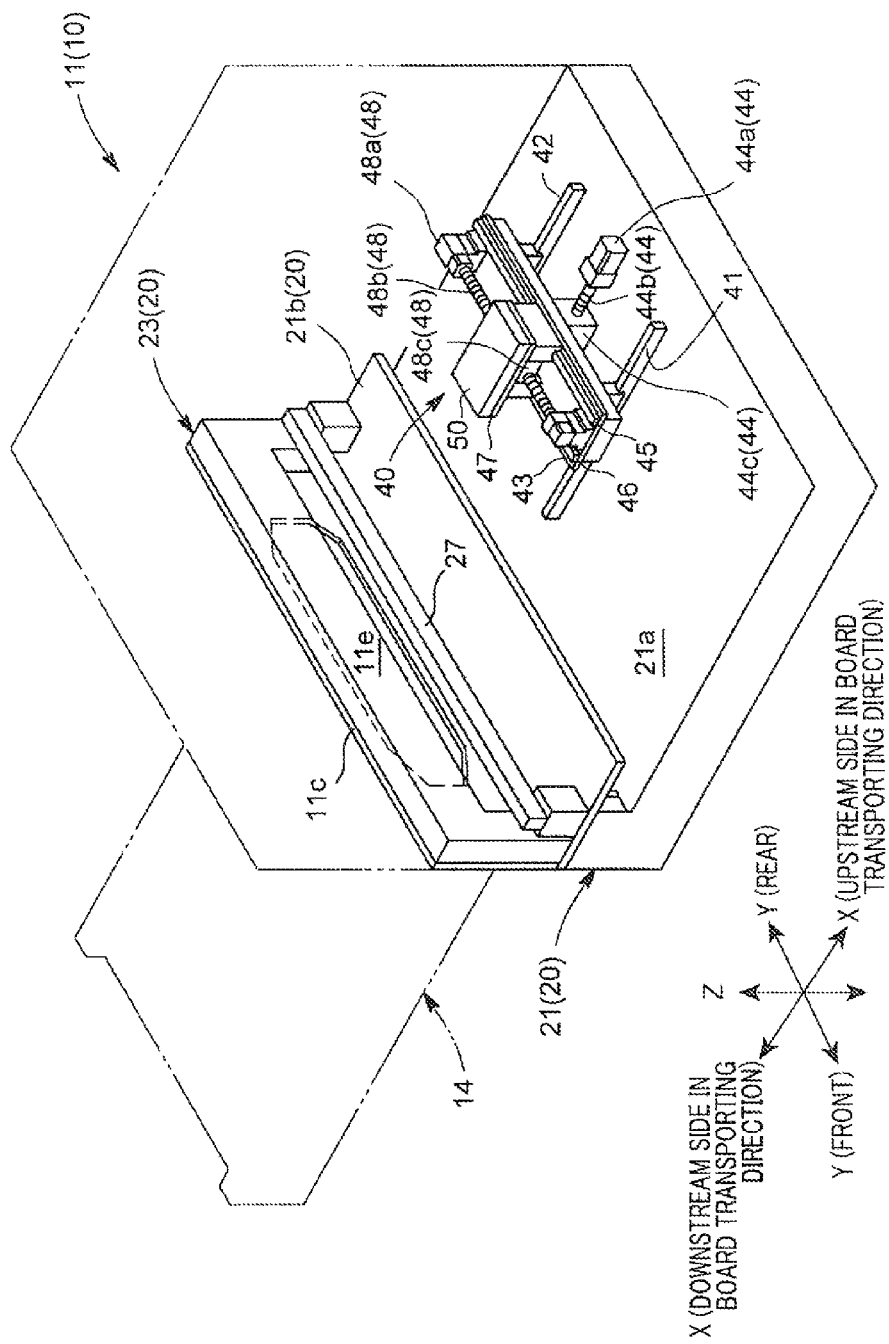
FIG. 3 is a perspective view depicting a general configuration of an X-ray camera unit that is used for the inspection machine according to first embodiment.

As shown in FIG. 3, the X-ray camera unit 40 has: a pair of X axis guide rails 41 and 42 which are secured to the bottom portion 21a of the base 21 and extend in the X axis direction respectively with a distance in the Y axis direction therebetween; an X axis slide table 43 which is guided by the X axis guide rails 41 and 42 and moves in the X axis direction; an X axis ball screw mechanism 44 which is disposed under the X axis slide table 43 and drives the X axis slide table 43 in the X axis direction; a pair of Y axis guide rails 45 and 46 which are secured on the top of the X axis slide table 43 as a pair, and extend along the Y axis direction respectively; a Y axis slide table 47 which is guided by the Y axis guide rails 45 and 46 and moves in the Y axis direction; a Y axis ball screw mechanism 48 which is disposed under the Y axis slide table 47 and drives the Y axis slide table 47 in the Y axis direction; and an X-ray camera 50 which is installed on the Y axis slide table 47.

The X axis guide rails 41 and 42 are disposed in an area slightly to the rear from the center part on the bottom portion 21a. In this position, the X axis guide rails 41 and 42 guide the X axis slide table 43 to move the X axis slide table 43 left and right along the X axis direction.

The X axis slide table 43 is formed to have a rectangular shape (plan view) that extends in the Y axis direction.

The X axis ball screw mechanism 44 has an X axis motor 44a which is installed on the bottom portion 21a, a ball screw 44b which is rotary driven by the X axis motor 44a, and a nut unit 44c which engages with the ball screw 44b, and is secured to the bottom face of the X axis slide table 43. The X axis ball screw mechanism 44 is constructed such that the X axis slide table 43 can move left and right along the X axis direction as the nut unit 44c moves in the X axis direction by rotation of the ball screw 44b.

The Y axis guide rails 45 and 46 extend substantially for the entire length of the X axis slide table 43 along the Y axis direction, with a space therebetween, in the width direction (X axis direction) of the X axis slide table 43. These Y axis guide rails 45 and 46 guide the Y slide table 47 along the Y axis direction so that the Y axis slide table 47 moves back and forth in the front and back directions.

The Y axis slide table 47 is a rectangular member of which length in the X axis direction is slightly longer in the plan view, and holds the X-ray camera 50 on the top face thereof. The X-ray camera 50 can therefore freely move in the front, back, left, and right directions (XY axis directions) on the bottom portion 21a by the movement of the X slide table 43 and the Y slide table 47. Since being installed on the Y axis slide table 47, the X-ray camera 50 protrudes slightly upward from the shelf portion 21b of the base 21.

The Y axis ball screw mechanism 48 has: a Y axis motor 48a which is installed at the rear end of the X axis slide table 43; a ball screw 48b which is rotary driven by this Y axis motor 48a; and a nut unit 48c which engages with the ball screw 48b and is secured to the bottom face of the Y axis slide table 47. The nut unit 48c moves along the Y axis direction as the ball screw 48b rotates, whereby the Y axis ball screw mechanism 48 moves the Y axis slide table 47 back and forth along the Y axis direction.

Figure 4:
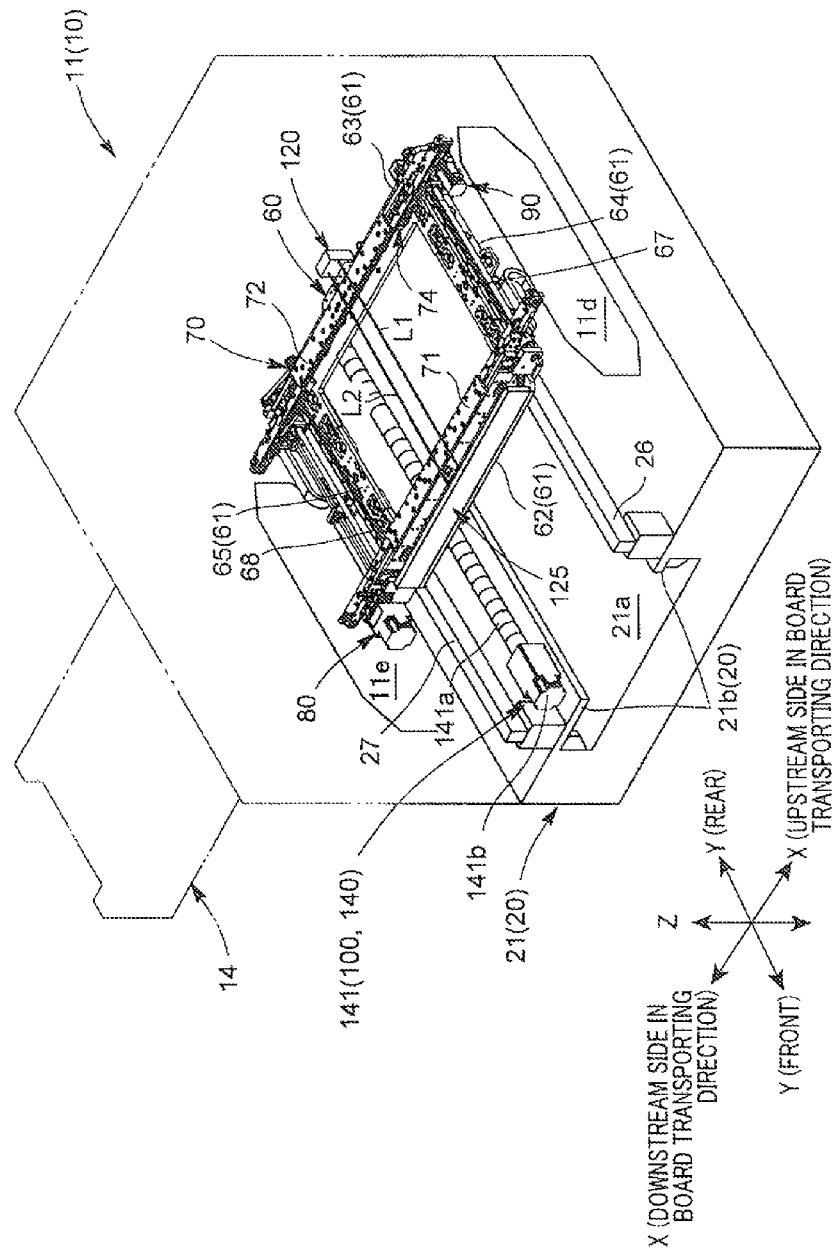
FIG. 4 is a perspective view depicting a general configuration of a board table used for the inspection machine according to first embodiment.
Figure 5:
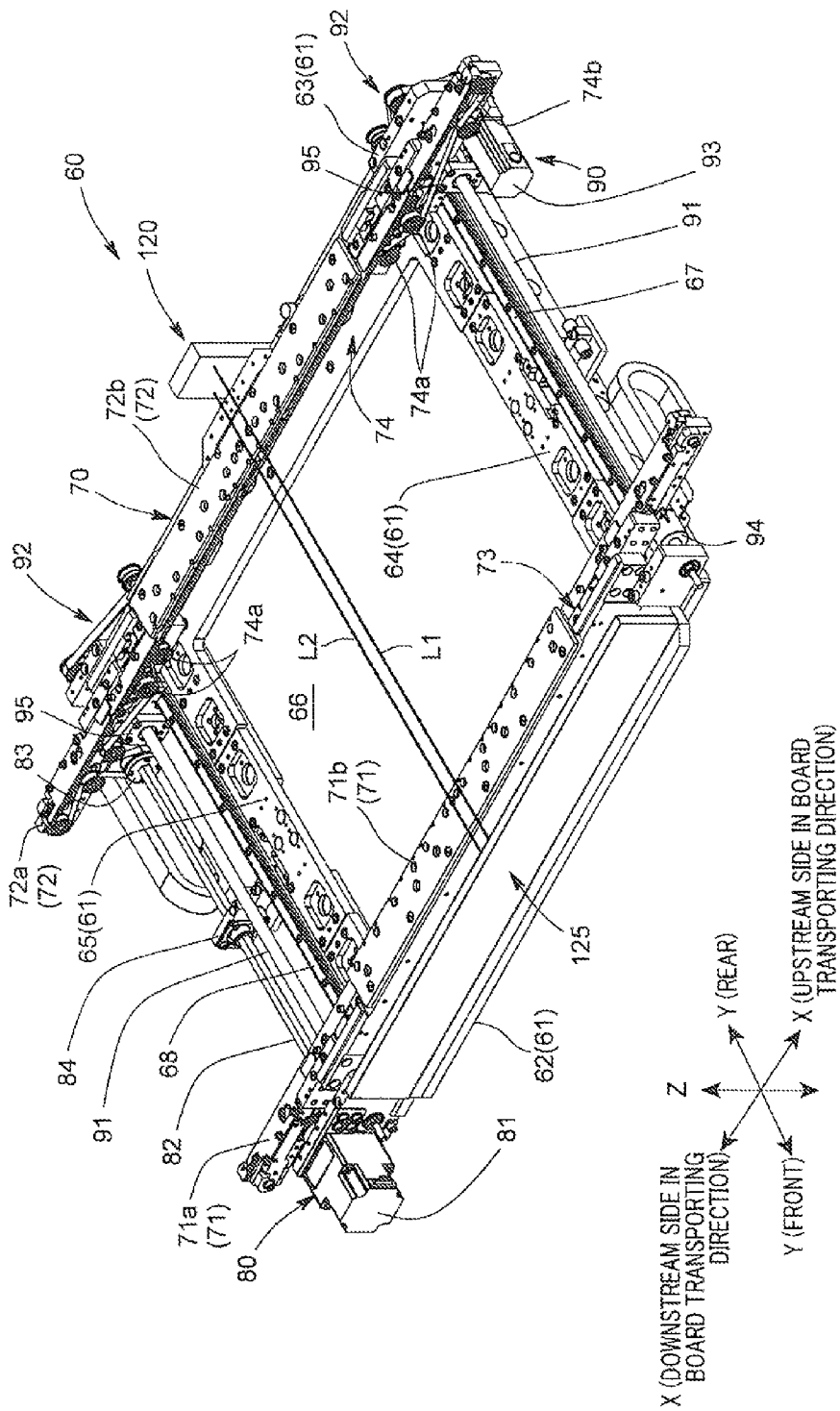
FIG. 5 is an enlarged perspective view of the board table in FIG. 4.
Figure 6:
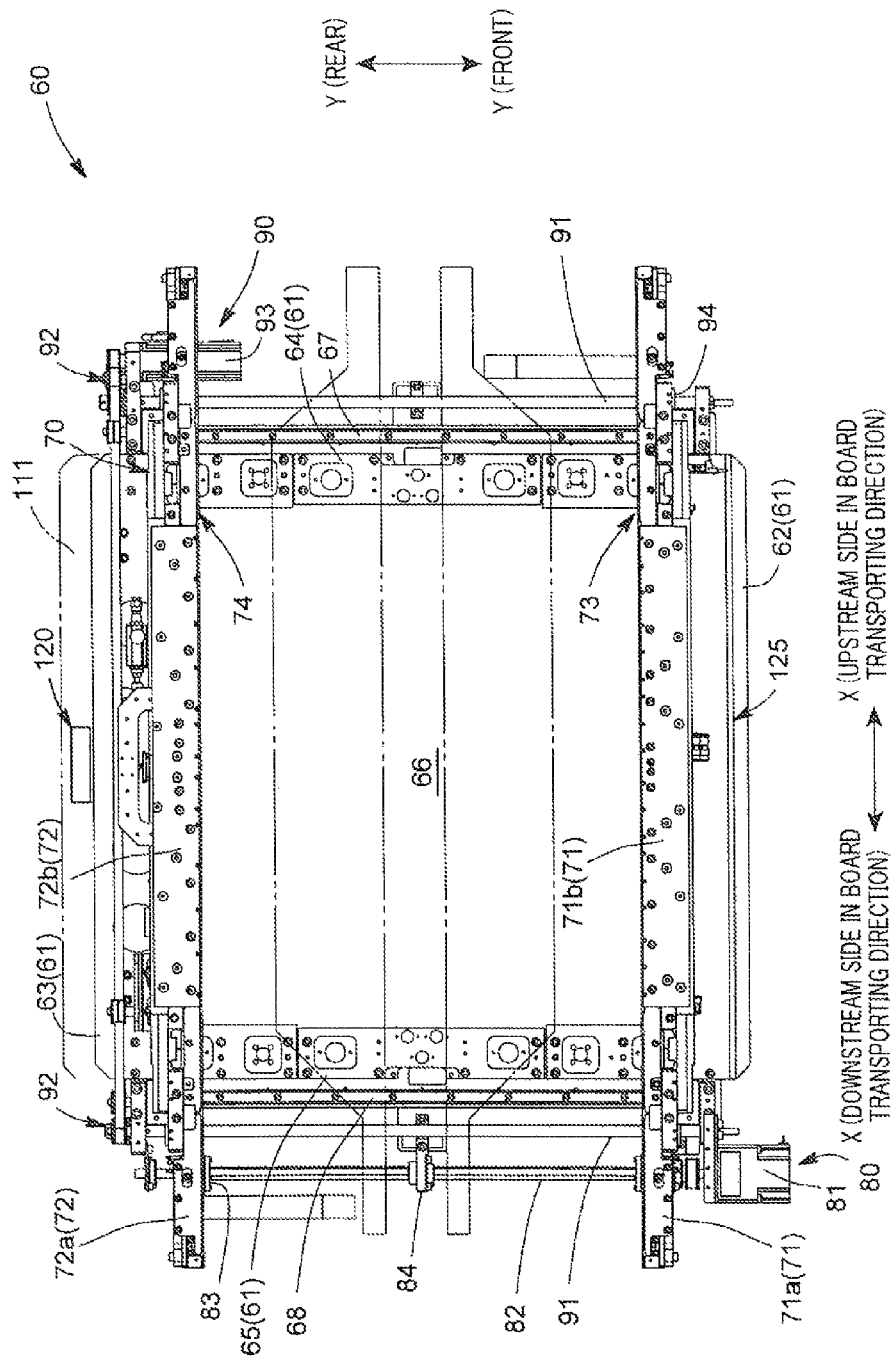
FIG. 6 is a plan view of the board table in FIG. 4.

As shown in FIGS. 4 to 6, the board table 60 has: a frame 61 which configures a main body portion; a conveyor unit 70 that transports/holds a printed circuit board W on the frame 61; a conveyor driving mechanism 80 that drives board conveyors 73 and 74 disposed on the conveyor unit 70; and a distance adjustment mechanism 90 that changes the facing distance of the conveyor unit 70. The inspection machine 10 of this embodiment also has a table driving mechanism 100 that drives the board table 60 in the X axis direction and Y axis direction.

The frame 61 is connected with a movable frame 111 of the table driving mechanism 100 which is described later, and is disposed to be movable in the XY axis directions. As illustrated, the frame 61 is square, integrating a pair of X axis pieces 62 and 63 which extend in the X axis direction and a pair of Y axis pieces 64 and 65 which are installed at both edges of the X axis pieces 62 and 63, extend in the Y axis direction. The frame 61 defines at the center of an opening 66 where an X-ray is transmitted.

Y axis rails 67 and 68 are secured respectively on the top faces of the Y axis pieces 64 and 65 of the frame 61. The conveyor unit 70 is installed on the Y axis rails 67 and 68. The conveyor unit 70 transports the printed circuit board W along the X axis direction.

The conveyor unit 70 has a pair of frame bodies 71 and 72 which are disposed at the front and back in the Y axis direction, the board conveyors 73 and 74 installed in each frame body 71 and 72, and a clamp unit (not illustrated) attached to one frame body (the frame body disposed at the rear side in the Y axis direction in the illustrated example) 72.

Each of the frame bodies 71 and 72 has X axis frames 71a and 72a, and fixing plates 71b and 72b. The X axis frames 71a and 72a extend in the X axis direction. The X axis frames 71a and 72a has edge protrudes from the frame 61. The fixing plates 71b and 72b are secured to the top face of the X axis frames 71a and 72a and of which side portion protrudes to the opening 66 side. The X axis frames 71a and 72a are guided by the Y axis rails 67 and 68 respectively, so that the X axis frames 71a and 72a can move to the front or back along the Y axis direction. Accordingly, each of the plates 71b and 72b move together with the corresponding X axis frames 71a and 72a along the Y axis direction.

The board conveyors 73 and 74 are configured by many rollers 74a and belt 74b. The rollers 74a are disposed along the corresponding surface of the frame bodies 71 and 72 facing each other. The belt 74b is wound around each roller 74a. In FIG. 5, the rollers and the belt of the board conveyor 73 on the front side are hidden, but have the same configurations as the roller 74a and the belt 74b of the board conveyor 74 on the rear side.

The clamp unit has an air cylinder for moving a rod in the Z axis direction, and a clamp that ascends/descends by the movement of the rod of the air cylinder, so that the clamp is elevated by the air cylinder and both ends of the printed circuit board W in the Y axis direction are virtually pinched and clamped between each fixing plate 71b and 72b of each frame body 71 and 72, and the clamp. When the printed circuit board W is clamped between each fixing plate 71b and 72b and the clamp by the clamp unit, the printed circuit board W is held in a position slightly lifted from a position where it is transported by the conveyor unit 70.

The conveyor driving mechanism 80 has a motor 81, a driving shaft 82, and an output pulley 83. The motor 81 is installed in one end (front side) of the frame body 61 in the X axis direction and outputs power around the Y axis. The driving shaft 82 is disposed between the board conveyors 73 and 74 along the Y axis direction and is rotary driven around the Y axis by the motor 81. The output pulley 83 is disposed for each of the board conveyors 73 and 74 so as to connect to the driving shaft 82, thereby outputting power to the belt 74b of the corresponding board conveyor 73 or 74 (only the output pulley 83 of the board conveyor 74 is illustrated). A cross-section of the driving shaft 82 driven by the motor 81 is formed in a polygon shape. Each output pulley 83 is therefore connected to the driving shaft 82 in a state of preventing the relative rotation with respect to the driving shaft 82 while being relatively movable along the Y axis direction. In the illustrated example, the driving shaft 82 is supported by a bearing 84 installed on the Y axis piece 65 of the frame 61, so that the driving shaft 82 rotates smoothly.

The distance adjustment mechanism 90 has double-end studs 91, a power transmit unit 92, and a motor 93. The double-end studs 91 are distributed both ends of the frame bodies 71 and 72 in the X axis direction. Each of the double-end studs 91 extends in the Y axis direction. The power transmit unit 92 is disposed on the rear face of the rear side frame body 72. The power transmit unit 92 transmits the torque to the double-end studs 91 in the same direction. The motor 93 is installed on the other end of the rear side frame body 72 in the X axis direction, and outputs the torque around the Y axis to the power transmit units 92. Each of the double-end studs 91 has right and left screws on both ends. These screws are symmetric with respect to the center portion of the double-end stud 91 in the Y axis direction. Nut mechanisms 94 and 95 are engaged with the right screw and the left screw of the double-end studs 91. The nut mechanisms 94 and 95 are respectively installed in the frame bodies 71 and 72. When the double-end stud 91 rotates in one direction (e.g. clockwise), the double-end stud 91 and the nut mechanisms 94 and 95 together move the frame bodies 71 and 72 in a direction to approach each other, as the virtual lines as shown in FIG. 6. When the double-end stud 91 rotates in the opposite direction (e.g. counterclockwise), the frame bodies 71 and 72 are moved in a direction to be apart from each other as the sold line as shown in FIG. 6.

Figure 9:
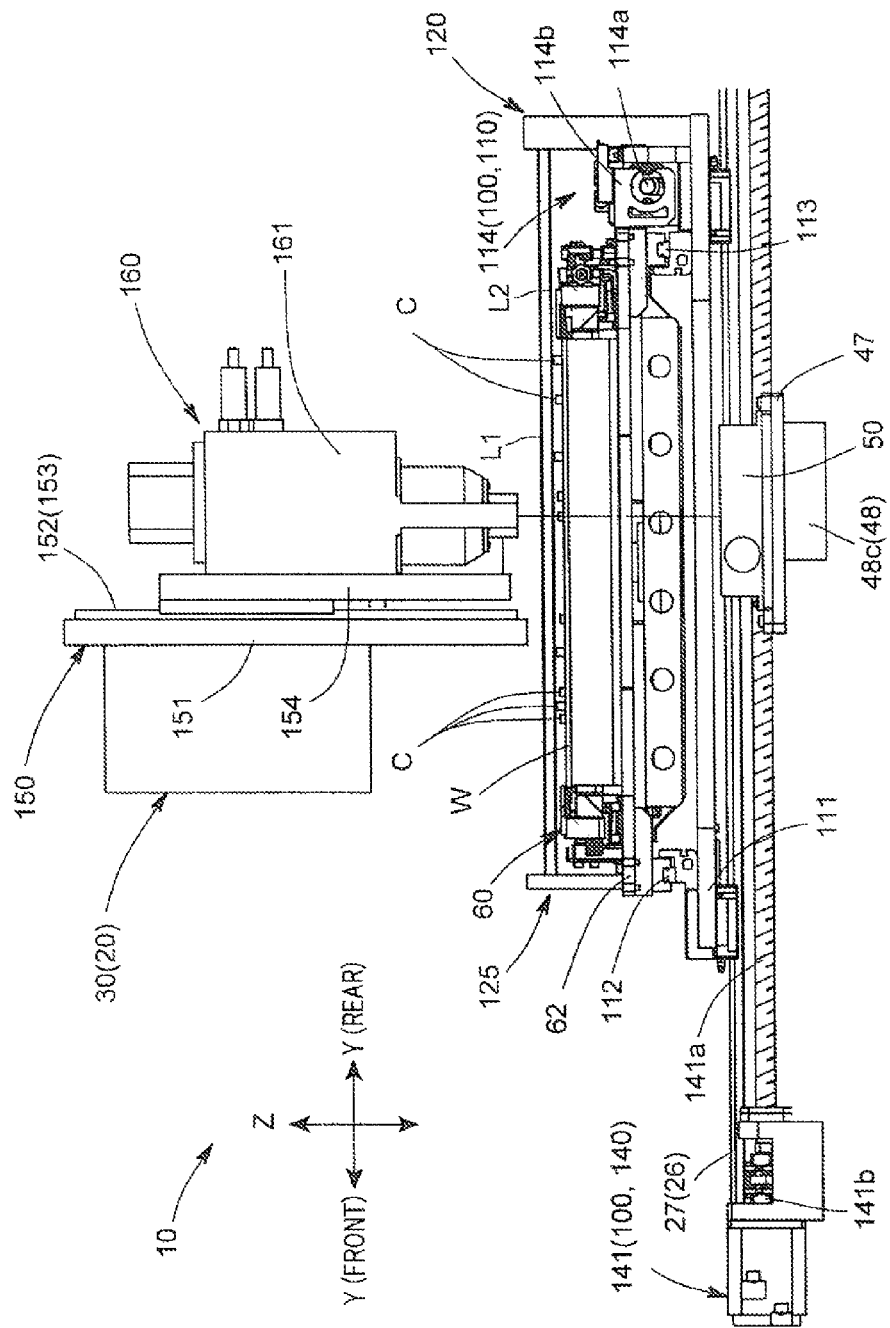
FIG. 9 is a schematic side view of a key portion of the inspection machine according to first embodiment.

As shown in FIGS. 4 and 9, the table driving mechanism 100 has an X axis driving mechanism 110 which drives the board table 60 in the X axis direction, and a Y axis driving mechanism 140 which drives the board table 60 in the Y axis direction via the X axis driving mechanism 110 (see FIG. 4).

The X axis driving mechanism 110 has a movable frame 111, a pair of X axis rails 112 and 113, and an X axis ball screw mechanism 114. The movable frame 111 is disposed on the bottom face of the frame 61 of the board table 60. Similar to the frame 61, the movable frame 111 is a frame type structure where the center portion is open. The X axis rails 112 and 113 are disposed on the movable frame 111 with a distance therebetween in the Y axis direction, so that these rails 112 and 113 guide the board table 60 in the X axis direction. The X axis ball screw mechanism 114 is installed behind the rear side X axis rail 113. The X axis ball screw mechanism 114 has a ball screw 114a which extends in the X axis direction, a nut portion (not illustrated) that engages with this ball screw 114a, and an X axis motor 114b which drives the ball screw 114a around the X axis. The nut portion is secured to the frame 61 of the board table 60, and receives the torque of the ball screw 114a and transforms into the force to relatively move the board table 60 in the X axis direction to the movable frame 111. Therefore, when the X axis motor 114b rotates and the ball screw 114a rotates, the board table 60 moves left and right along the X axis direction by the force in the X axis direction received from the nut portion.

As shown in FIG. 4, the Y axis driving mechanism 140 has the above mentioned pair of Y axis rails 26 and 27 which are disposed on the shelf portions 21b, and a Y axis ball screw mechanism 141 which is disposed at the inner side of the Y axis rail 26 at the downstream side of the board traveling direction in the X axis direction (side facing the Y axis rail 27 at the upstream side of the board traveling direction in the X axis direction). The Y axis rails 26 and 27 respectively guide the movable frame 111, so that the movable frame 111 moves back and forth in the Y axis direction. The Y axis balls screw mechanism 141 has a ball screw 141a, a nut portion (not illustrated), and a Y axis motor 141b. The ball screw 141a extends in the Y axis direction. The nut portion engages with this ball screw 141a. The Y axis motor 141b rotary drives the ball screw 141a. The ball screw 141a is supported by a bearing (not illustrated) so as to rotate freely on the shelf portion 21b. The nut portion is secured to the bottom face of the movable frame 111, and receives the torque of the ball screw 141a. If the torque is received, the nut portion transforms into the force for driving the board table 60 in the Y axis direction via the movable frame 111. Therefore if the Y axis motor 141b rotates and the ball screw 141a rotates, the board table 60, which receives the force in the Y axis direction from the nut portion, moves back and forth in the Y axis direction via the movable frame 111.

To detect the heights of the electronic components on the printed circuit board W held by the board table 60, a sensor unit 120 is installed on the movable frame 111, in this embodiment.

As shown in FIGS. 4 to 7, the sensor unit 120 is in a box type case 121, in which two reflection type photoelectric switches 120A and 120B are installed. The case 121 is vertically installed approximately at the center on the rear side frame piece of the movable frame 111. Each photoelectric switch 120A and 120B has a light emitting portion 122 and a light receiving portion 123, respectively. These photoelectric switches 120A and 120B both face the front side of the board table 60 when the sensor unit 120 is assembled. In a reduction to practice, any light in various wavelength regions such as visible light, ultraviolet, infrared, or the like may be used, provided that the photoelectric switches 120A and 120B enable detecting the heights of the electronic components on the printed circuit board W. Change of any "lights" from a standard lamp, an LED, laser beam, and so forth may also be utilized. In description, these various lights that the photoelectric switches 120A and 120B irradiate are generically called "irradiation light". In this embodiment, the irradiation light is irradiated in the Y axis direction along the surface of the board table 60. In other words, in this embodiment, the Y axis direction is the first direction. Also in this embodiment, the board transporting direction (X axis direction) is the second direction.

In order to reflect the light irradiated by the light emitting portions 122 of each photoelectric switch 120A and 120B to the light receiving portions 123, a mirror 125 is vertically installed on the X axis piece 62 on the front side of the board table 60. The mirror 125 extends over substantially the entire length of the opening 66 along the X axis direction. As mentioned above, in this embodiment, the X axis driving mechanism 110 enables moving the board table 60, which holds the printed circuit board W on the movable frame 111, left and right along the X axis direction. During this left and right movement, the irradiation light L1 and L2 irradiated from the light emitting portion 122 of each photoelectric switch 120A and 120B is irradiated onto the side of electronic components. The light reflected by the mirror 125 and is then received by the light receiving portion 123, whereby the height of the electronic components can be detected throughout the entire length of the printed circuit board W in the X axis direction.

Figure 7:
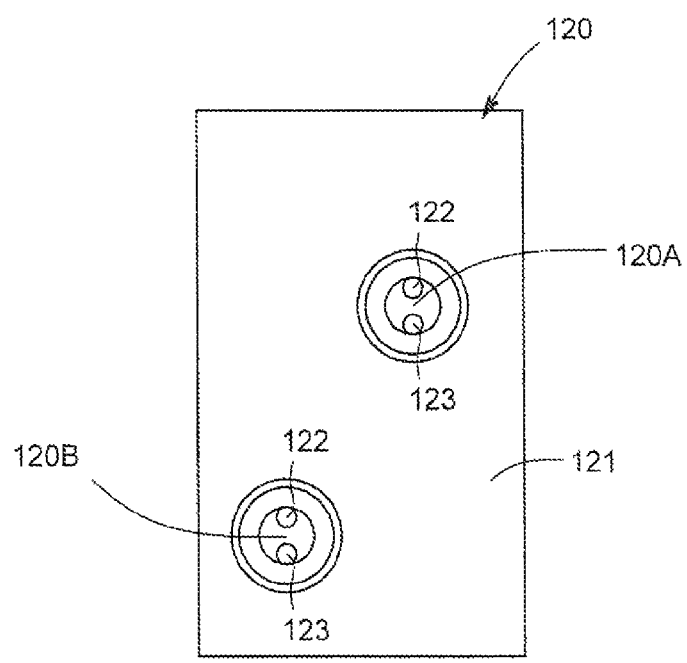
FIG. 7 is a schematic front view of the detection means used for the inspection machine according to first embodiment.

As shown in FIG. 7, the heights at which the photoelectric switches 120A and 120B are disposed in different height. The upper photoelectric switch 120A is an example of the "intermediate sensor" of the present invention. The lower photoelectric switch 120B is an example of the "bottom sensor" of the present invention.

Figure 8:
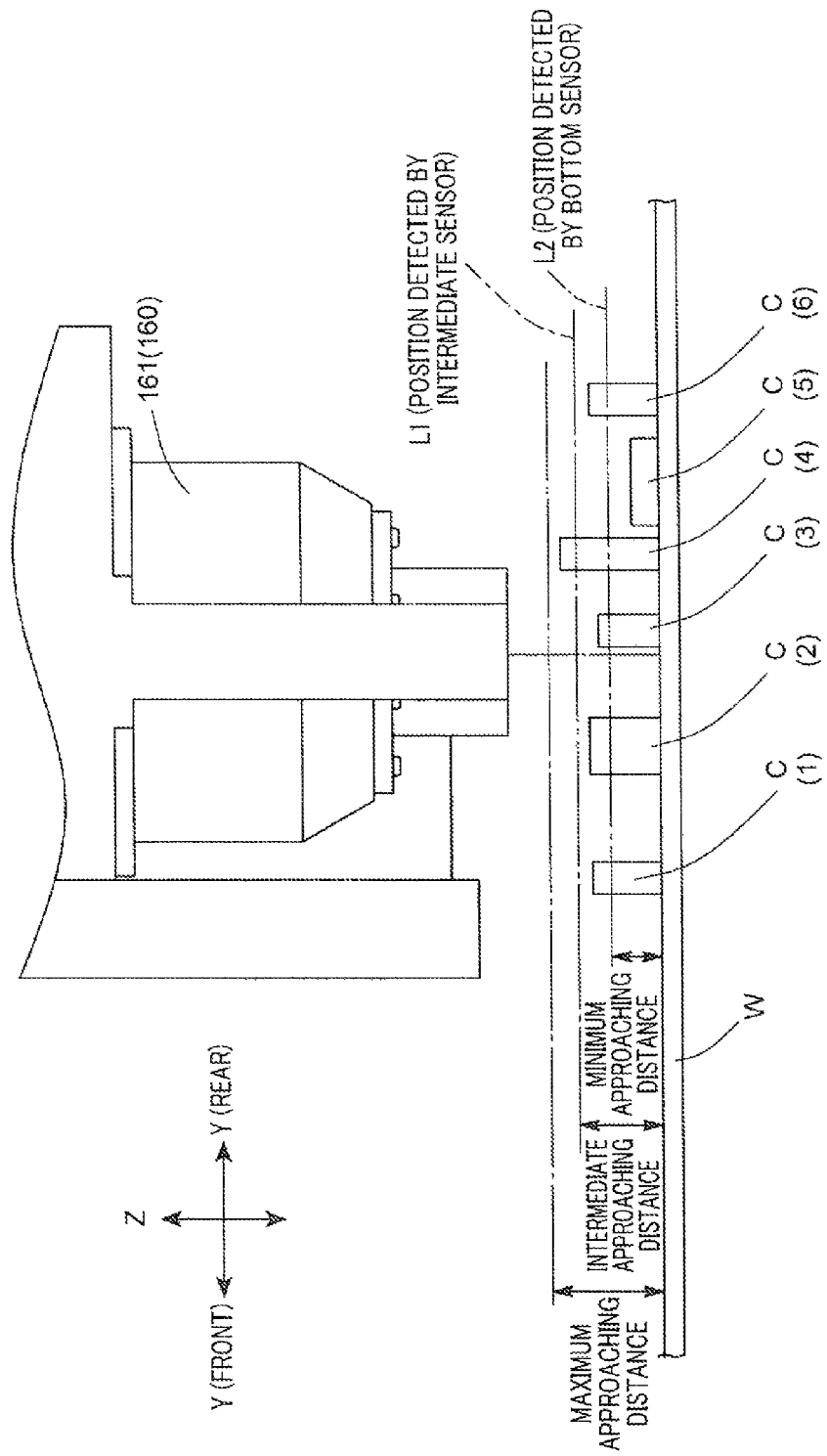
FIG. 8 is a partial schematic side view of the inspection machine according to first embodiment, where a key portion is enlarged.

As shown in FIG. 8, according to this embodiment, minimum, maximum, and intermediate distances are set in advance. The minimum approaching distance is a facing distance by which an imaging device are accepted to approach the shortest electronic component C (electronic component C (5) in the case of FIG. 8) among the electronic components C mounted on the printed circuit board W to be subjected to inspections. The maximum approaching distance is a facing distance by which an imaging device are accepted to approach the highest electronic component C (electronic component C (4) in the case of FIG. 8) among the electronic components mounted on the printed circuit board W to be subjected to inspections. The intermediate approaching distance is a facing distance between the maximum approaching distance and the minimum approaching distance.

The photoelectric switch 120A, as the intermediate sensor, is installed in a position to detect electronic components C at a height corresponding to the intermediate approaching distance (electronic component C (4) in the case of FIG. 8). The photoelectric switch 120B, as the bottom sensor, is installed in a position to detect electronic components C at a height corresponding to the minimum approaching distance (electronic component C other than (5) in the case of FIG. 8). Based on the detection result by these photoelectric switches 120A and 120B, the control unit 600 of the inspection machine 10 restricts the height by which the imaging device, or an X-ray irradiation unit 160 are accepted to approach the printed circuit board W. This height is set to a position higher than the highest electronic component (electronic component C (4) in the case of the illustrated example) among the electronic components C, that is the maximum approaching distance in the case of the illustrated example.

For the sensor unit 120 to scan the printed circuit board W, the control unit 600 drives the X axis driving mechanism 110 of the table driving mechanism 100 and moves the printed circuit board W and the sensor unit 120 relatively in the X axis direction by the X axis driving mechanism 110. Specifically, the X axis ball screw mechanism 114 of the X axis driving mechanism 110 is activated, and the board table 60 is moved left and right on the movable frame 111. During this movement, the printed circuit board W and the sensor unit 120 are relatively moved, so that the sensor unit 120 can scan the surface of the printed circuit board W over the entire length of the printed circuit board W in the X axis direction. In this embodiment, the X axis driving mechanism 110 is an example of the "displacement means" or the "driving means which serves functions as the displacement means".

The X-ray irradiation unit (an example of a composing element of the imaging device) 160 for performing transmission inspection on a printed circuit board W held on the board table 60 will be described next. The X-ray irradiation unit 160 is supported by an X-ray source support mechanism 150 which can change the magnification of the X-ray image by moving the X-ray source up or down. Therefore, the X-ray source support mechanism 150 will be described first.

As shown in FIG. 9, the X-ray source support mechanism 150 has a support plate 151 which is a plate secured to the rear face of the beam 30, a pair of elevation rails 152 and 153 which are secured to the rear face of the support plate 151 and extend in the Z axis direction, an elevation slider 154 which is linked with the elevation rails 152 and 153, and a ball screw mechanism (not illustrated) which vertically drives the elevation slider 154. The support plate 151 is a sheet metal member constituting the structure 20, along with the beam 30, and is firmly secured to the beam 30 in the case of the illustrated example. In the support plate 151, a stopper (not illustrated) is installed, and the elevation slider 154 is guided to ascend/descend in the Z axis direction in the stroke range specified by the stopper. The stroke range is determined based on a magnification required for the X-ray image of the inspection machine 10 within the range specified by the control unit 600.

The inspection machine 10 of this embodiment irradiates an X-ray onto the printed circuit board W at a predetermined evaluation angle (e.g. 45°), and executes capturing from diagonal view to capture an inspection target portion in a diagonal direction. For capturing this imaging from diagonal view, a close-up position is set as constraint conditions in the control unit 600. Furthermore, in the imaging from diagonal view, the printed circuit board W can be moved on the plane of the housing 11 in a wide range using the table driving mechanism 100.

Next, the X-ray irradiation unit 160 has a known configuration, provided with a housing 161, a high voltage generation unit (not illustrated) stored inside the housing 161, and an X-ray irradiation unit that irradiates the X-ray with power supplied from the high voltage generation unit.

In order to capture an X-ray diagonal imagines of the printed circuit board W taken from predetermined number of elevation angles among all directions, the table driving mechanism 100 controls the movement of the board table 60 in the X axis direction and the Y axis direction, and controls the movement of the X-ray camera 50 in the X-ray camera unit 40 in the X axis direction and the Y axis direction.

The inspection machine 10 includes control unit 600 that controls the all devices.

Figure 10:
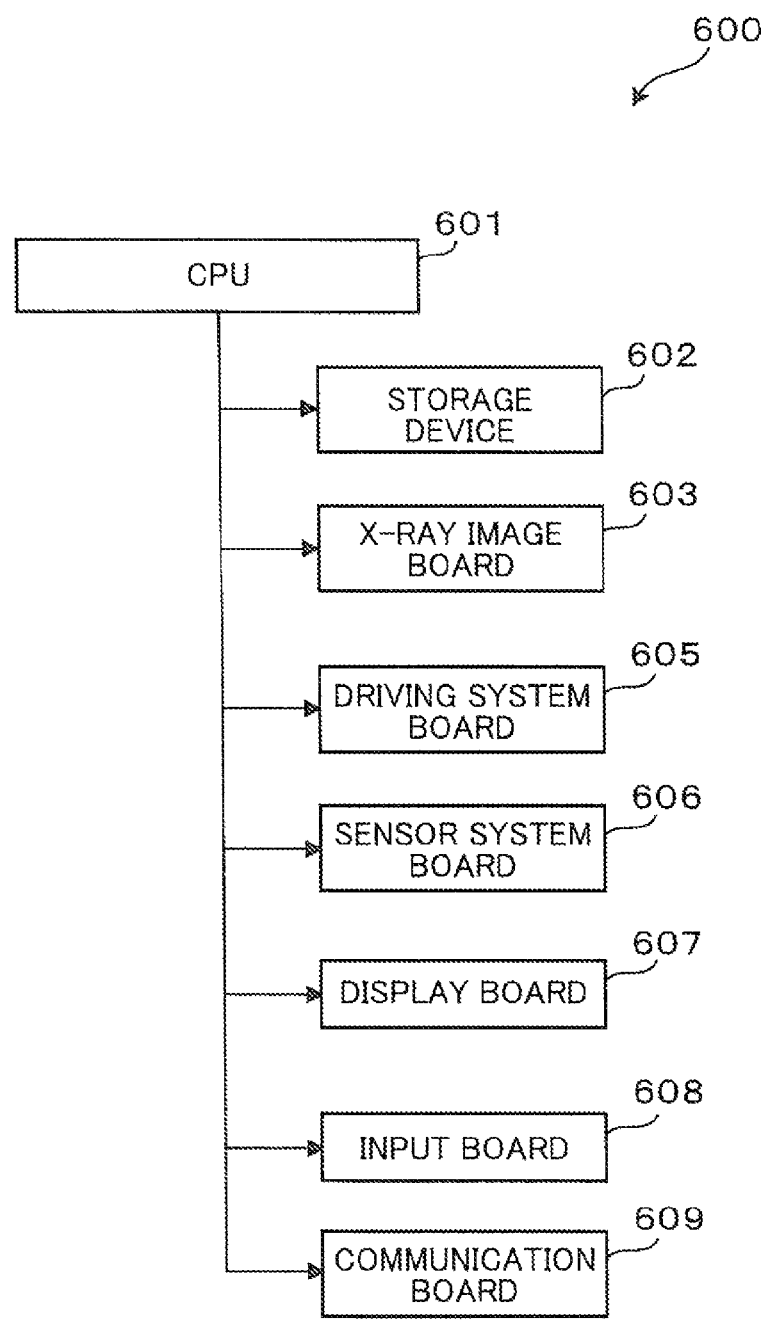
FIG. 10 is a block diagram depicting a general configuration of control means of the inspection machine according to first embodiment.

As shown in FIG. 10, the control unit 600 has a main control unit (CPU) 601 which is in the form of a microprocessor, for example, and to this main control unit 601, a storage device 602, an X-ray image board 603, a driving system board 605, a sensor system board 606, a display board 607, an input board 608, and a communication board 609 among others are connected.

The storage device 602 includes a ROM, RAM, an auxiliary storage device or the like, and stores, for example, programs and master data required for controlling each unit of the inspection machine 10 and executing inspections, master data on the printed circuit board W to be subjected to inspections, packaged components, inspection items and inspection target products, and transaction data which define inspection specifications for the inspection target items. In this storage device 602, the set values of the minimum approaching distance, the maximum approaching distance, and the intermediate approaching distance described in FIG. 8 are stored in advance. The storage device 602 is an example of the "storage means" or "storage unit" of the present invention. Specifically, the minimum approaching distance may set to a distance (e.g. 9 mm) to avoid interference with a 6.5 mm high electronic component. The maximum approaching distance is set to a distance (e.g. 50 mm) to avoid interference with a 40 mm high electronic component. The intermediate approaching distance is set to a distance (e.g. 25 mm) to avoid interference with a 15 mm high electronic component.

The X-ray image board 603 is an interface to connect the X-ray camera 50 to the main control unit 601, and through this X-ray image board 603, the main control unit 601 can execute the transmission inspection for the inspection target product based on the X-ray image captured by the X-ray camera 50.

The driving system board 605 is an interface to connect various motors (e.g. each X axis motor 44a, 141b, 114b, 144b, 155b, 185b, or the like of the ball screw mechanism 44, 114, 141, 155 and 185) installed in the inspection machine 10, and the actuator of the clamp unit, to the main control unit 601, and through this driving system board 605, the main control unit 601 can control the rotation direction, rotation amount, rotation speed, operation timing or the like of the various motors, or can control the switching operation of the air cylinder of the clamp unit.

The sensor system board 606 is an interface to connect various sensors installed in the inspection machine 10 to the main control unit 601, and through this sensor system board 606, the main control unit 601 can detect the operation timing of each unit and the presence of the printed circuit board W based on the detection result detected by the various sensors. The signal detected by each photoelectric switch 120A and 120B of the sensor unit 120 described above is transmitted to the main control unit 601 via this sensor system board 606. The main control unit 601 controls the ascending/descending amount of the X-ray irradiation unit 160 based on the detection by each photoelectric switch 120A and 120B.

The display board 607 or a graphic card is an interface to connect the display panel 610 and the lamp 611 installed on the front face of the inspection machine 10 to the main control unit 601, and through this display board 607, the main control unit 601 can display the control information on the display panel 610 using the graphical user interface (GUI), or flash the lamp 611 disposed on the top of the inspection machine 10 (see FIG. 1).

The input board 608 is an interface to connect a pointing device, such as a keyboard 620 installed on the front face of the inspection machine 10 to the main control unit 601, and through this input board 608, the main control unit 601 can receive data, such as the data generated by the user operating the keyboard 620.

The communication board 609 is for executing data communication with a host computer which manages the production programs of a facility where the inspection machine 10 is installed, and through this communication board 609, the main control unit 601 is connected to the host computer via LAN and/or WAN, and can obtain information on the inspection target items, such as an item number of the printed circuit board W to be subjected to inspections.

Figure 11:
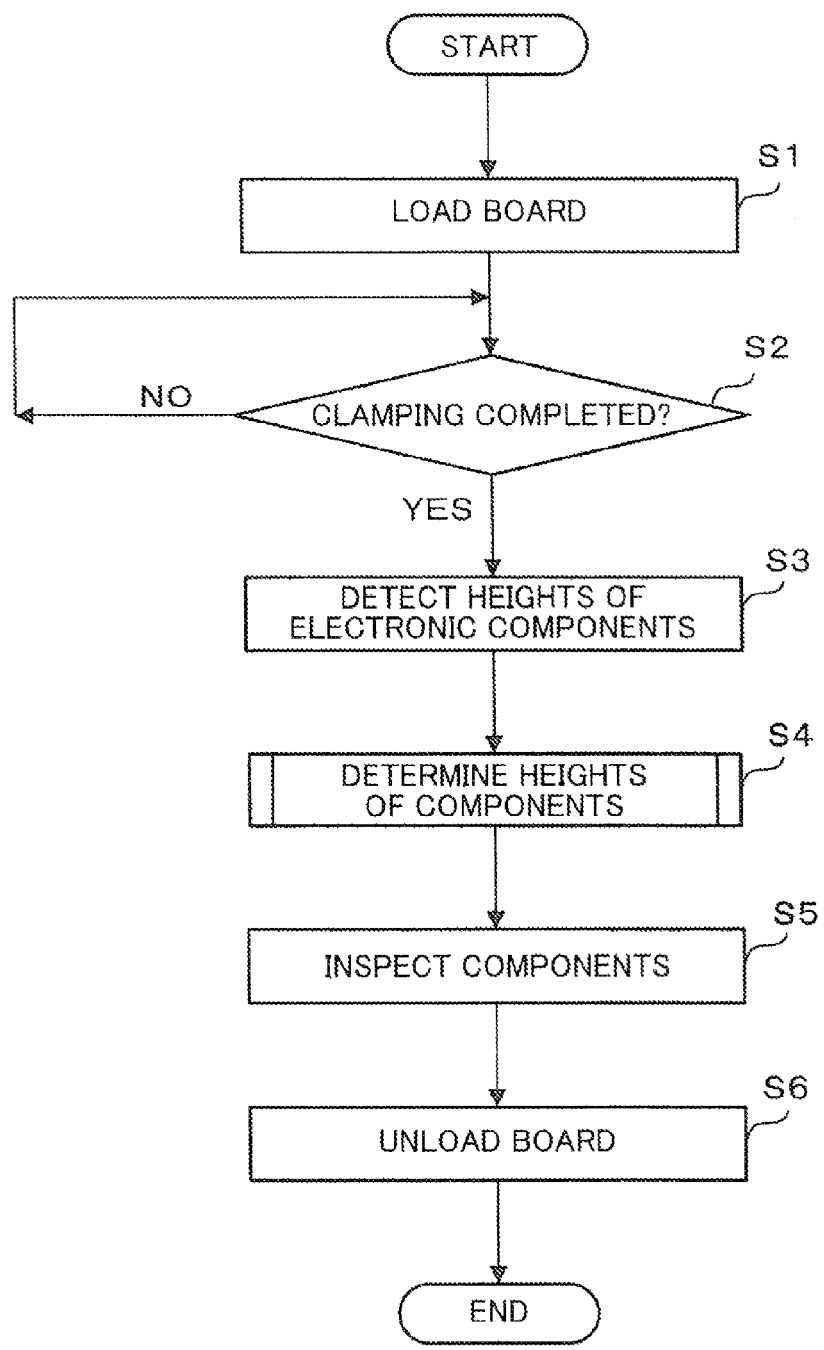
FIG. 11 is a flow chart depicting an operation of the inspection machine according to first embodiment.

The main control unit 601 controls each unit of the inspection machine 10 according to the following procedure, based on the programs stored in the storage device 602. FIG. 11 is a flow chart showing the steps of inspecting one printed circuit board W as one unit.

As shown in FIG. 11, a board loading processing (step S1) for loading the printed circuit board W into the housing 11 of the inspection machine 10 is executed first.

In the board loading step in step S1, the printed circuit board W which has been completed upstream steps is transported by the board conveyor 12. When the transported printed circuit board W is detected, the control unit 600 opens the shutter mechanism of the opening 11*d* as a board loading entrance to open the opening 11*d*, and receives the printed circuit board W. In this case, the board table 60 is driven by the X axis motor 114*b* of the X axis ball screw mechanism 114, and moves toward the opening 11*d* and receives the printed circuit board W loaded by the board conveyor 12. In case the inspection machine 10 is used in a multi-item small lot production environment, the widths of the printed circuit boards W to be loaded vary. In this board loading step, the distance adjustment mechanism 90 of the board table 60 is activated, so as to adjust the facing distance between the frame bodies 71 and 72 of the conveyor unit 70 to a size matching with the width of the printed circuit board W to be loaded, based on the communication data which has been obtained from the host computer in advance. The printed circuit board W loaded through the opening 11*d* is placed onto the board table 60 by the conveyor driving mechanism 80 of the conveyor unit 70.

After loading, the shutter mechanism at the loading side is activated and the opening 11*d* closes again so that the X-ray during X-ray imaging does not leak.

By control of the control unit 600, the loaded printed circuit board W moves to a predetermined position, where the printed circuit board W is clamped and held between the frame bodies 71 and 72 of the conveyor unit 70. At this time, the control unit 600 monitors the timing when the clamping completes (step S2). When the clamping completes (YES in step S2), the control unit 600 detects the height of the electronic components C on the printed circuit board W (step S3). In step S3, the control unit 600 activates the X axis motor 114*b* of the X axis ball screw mechanism 114. As an operation of the board table 60, the board table 60 once moves out toward the opening 11*e* which is the board unloading exit, then returns toward the opening 11*d* which is the board loading entrance, for example. In this example, the sensor unit 120 can detect the heights of the electronic components C on the printed circuit board W at a timing when the board table 60 returns. If the sensor unit 120 completes scanning of the printed circuit board W for the entire length of the printed circuit board W in the X axis direction, the control unit 600 moves the board table 60 out to the opening 113 again, if necessary, and places the printed circuit board W at a required position for X-ray imaging. Needless to say, the sequence of the operation of the board table 60 may be reversed. In other words, the board table 60 is once returned to the opening 11*d* side. Then the board table 60 is moved out to the opening 11*d* side. The sensor unit 120 detects the heights of the electronic components C on the printed circuit board W at a timing when the board table 60 is moved out. According to this embodiment, the sensor unit 120 detects the heights of the electronic components C after loading of the printed circuit board W completes and the printed circuit board W is held on the board table 60, therefore the heights of the electronic components C can be accurately detected, even if there is a difference between the height of the printed circuit board W when loading, and the height of the printed circuit board W when being clamped.

When the detection of the heights of the electronic components C is terminated, the control unit 600 then executes a component height determination sub-routine (step S4). By this sub-routine, the closest distance by which the X-ray irradiation unit 160 is accepted to approach the printed circuit board W (hereafter called "limit distance") is set. In other words, the control unit 600 sets the limit distance to a position higher than the highest electronic component C (electronic component C (6) in the case of FIG. 8) out of the electronic components C of which heights have been detected.

Figure 12:
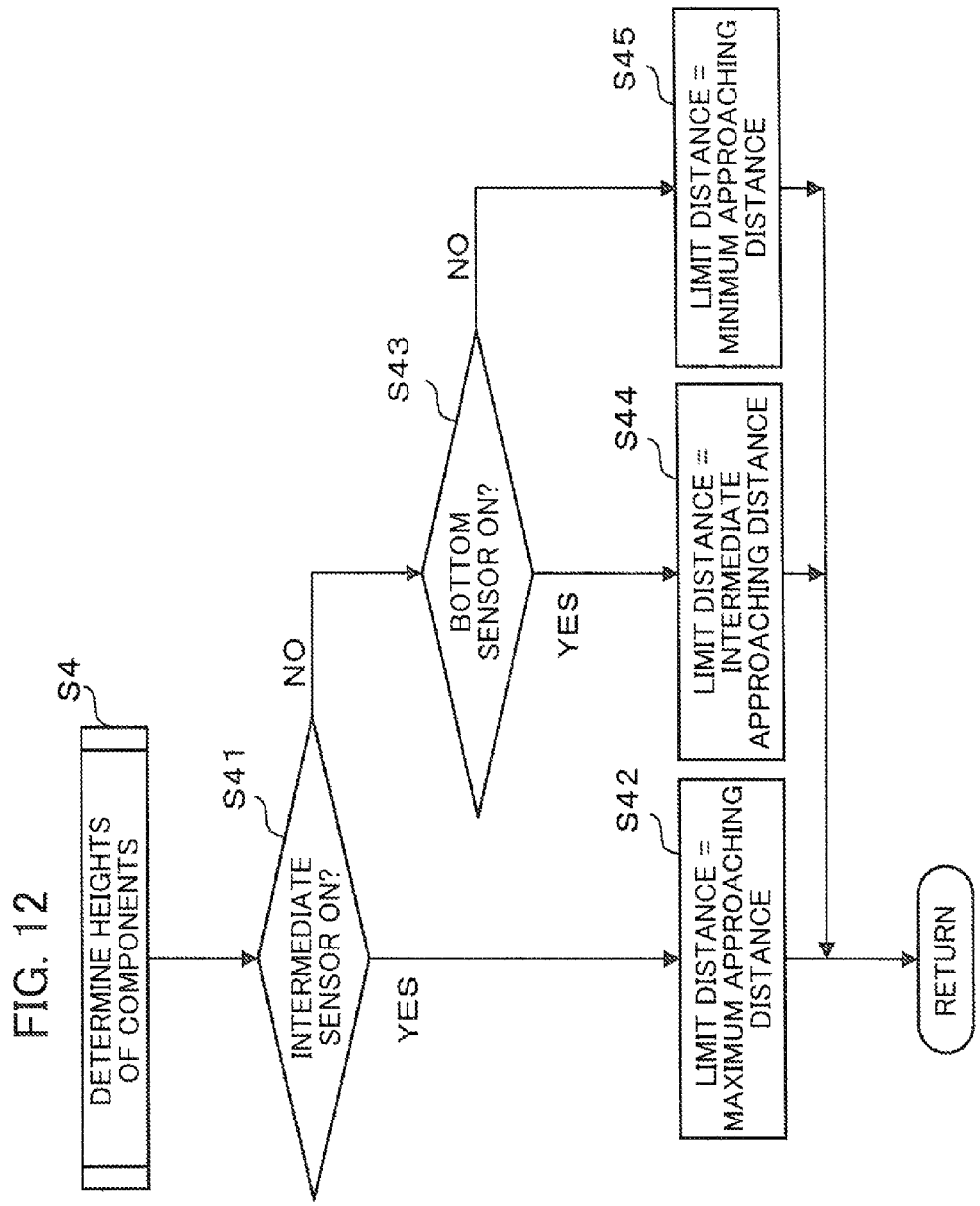
FIG. 12 is a flow chart depicting a sub-routine of the flow chart in FIG. 11.

As shown in FIG. 12, the detection state of the photoelectric switch 120A as the intermediate sensor is initially determined (step S41) in the component height determination sub-routine (step S4). If this photoelectric switch 120A is in the ON state, that is, if the photoelectric switch 120A detects the electronic components C, the limit distance is set to the maximum approaching distance shown in FIG. 8 (step S42). On the other hand, if the photoelectric switch 120A as the intermediate sensor is in the OFF state, that is, if the photoelectric switch 120A does not detect the electronic components C, in the determination in step S41, the control unit 600 determines the detection state of the photoelectric switch 120B as the bottom sensor (step S43). If the photoelectric switch 120B is in the ON state, that is, if the photoelectric switch 120B detects the electronic components C, in the determination in step S43, the limit distance is set to the intermediate approaching distance shown in FIG. 8 (step S44). On the other hand, if the photoelectric switch 120B as the bottom sensor is in the OFF state, that is, if the photoelectric switch 120B does not detect the electronic components C, in the determination in step S43, the limit distance is set to the minimum approaching distance shown in FIG. 8 (step S45). After executing step S42, S44 or S45, the control unit 600 ends the component height determination sub-routine (step S4), and returns to the main routine.

Then the control unit 600 moves to the component inspection step (step S5). In this component inspection step, the X-ray irradiation unit 160 and the X-ray camera unit 40 execute transmission imaging of the inspection target portion of the printed circuit board W, and execute close-up imaging, if necessary. If close-up imaging is performed, the heights by which the X-ray irradiation unit 160 is accepted to approach is restricted to a position above the highest electronic component C (electronic component C (4) in the case of FIG. 8) determined by the sensor unit 120, hence the X-ray irradiation unit 160 and the electronic components C will never interfere with each other.

If the imaging is terminated, the control unit 600 executes the processing to move the printed circuit board W after the inspection to the unloading position (step S6). In this unloading movement operation, the X axis driving mechanism 110 of the table driving mechanism 100 is activated again, and the board table 60 is driven to the downstream side in the board transporting direction (direction toward the opening 11e in the case of the illustrated example, see FIG. 2, etc. along the X axis direction). If the board table 60 comes to the opening 11e as the board unloading exit, and the movement of the board table 60 stops, then clamping of the board table 60 is released, and the unloading operation is executed. In this unloading operation, the shutter mechanism on the unloading side is activated and opens the opening 11e. Then the conveyor driving mechanism 80 activates the board conveyors 73 and 74 and unloads the inspected printed circuit board W to the board conveyor 14 on the unloading side. After unloading, the shutter mechanism is activated and the opening 11e is closed, and in order to move to the next operation, the X axis driving mechanism 110 of the table driving mechanism 100 is activated again, and the board table 60 is driven to the upstream side in the board transporting direction (direction toward the opening 11d in the case of the illustrated example, see FIG. 2, etc. along the X axis direction).

As described above, according to first embodiment, the heights of the electronic components C mounted on the printed circuit board W are detected before the X-ray camera unit 40 and the X-ray irradiation unit 160, which are examples of the imaging device execute imaging. In order to prevent interference with the electronic components C, the height, by which the X-ray camera unit 40 and the X-ray irradiation unit 160 or the imaging device enable approaching to the printed circuit board W, is restricted to the height corresponding to the highest electronic component C among heights detected from the electronic components C. Thus the interference between the X-ray irradiation unit 160 as a part of imaging device and the electronic components C mounted on the printed circuit board W can be surely prevented. To detect the heights of the electronic components C here, the irradiation lights L1 and L2 of the sensor unit 120 or detection means are irradiated in a first direction that is along the surface of the printed circuit board W held by the board table 60. At the same time, the driving mechanism 100 moves the sensor unit 120 and the printed circuit board W relatively in a second direction, which is along the surface of the printed circuit board W and crosses the first direction. Due to the relative movement of the sensor unit 120 and the printed circuit board W, the entire surface of the printed circuit board W is scanned, and the heights of all the electronic components C mounted on the printed circuit board W can be detected. The "direction along the surface" is preferably the direction parallel with the surface, but may have an inclination small enough not to cross the printed circuit board W. The "direction to cross" is preferably to cross orthogonally, or perpendicularly. However, this need not be exactly orthogonal if the entire surface of the printed circuit board W can be scanned.

According to this embodiment, the inspection machine also has a storage device 602 as storage means for storing a minimum approaching distance that is preset as a facing distance by which the X-ray irradiation unit 160 is accepted to approach the shortest electronic component C (electronic component C (5) in the case of FIG. 8) among the electronic components C mounted on the printed circuit board W to be subjected to inspections, a maximum approaching distance that is preset as a facing distance by which the X-ray irradiation unit 160 is accepted to approach the highest electronic component C (electronic component C (4) in the case of FIG. 8) among the electronic components C mounted on the printed circuit board W to be subjected to inspections, and an intermediate approaching distance that is preset as a facing distance between the minimum approaching distance and the maximum approaching distance. The sensor unit 120 includes the photoelectric switch 120B as the bottom sensor that detects the heights of the electronic components C mounted on the printed circuit board W to be subjected to inspections at a height corresponding to the minimum approaching distance, and the photoelectric switch 120A as the intermediate sensor that detects the heights of the electronic components C at a height corresponding to the intermediate approaching distance. Therefore according to this embodiment, as shown in the flow chart in FIG. 12, the heights of the electronic components C corresponding to the various facing distances are detected by the two photoelectric switches 120A and 120B, therefore the facing distance by which the X-ray irradiation unit 160 as the imaging device is accepted to approach the printed circuit board W can be determined in steps. As a result, unnecessarily strict restriction for the close-up function of the imaging device can be avoided.

Particularly in this embodiment, the control unit 600 sets the limit distance to the maximum approaching distance when the photoelectric switch 120A detects the electronic components C at the intermediate approaching distance. The control unit 600 also sets the distance to the intermediate approaching distance when the photoelectric switch 120A does not detect the electronic components C at the intermediate approaching distance while the photoelectric switch 120B detects the electronic components C at the minimum approaching distance. Also the control unit 600 sets the limit distance to the minimum approaching distance when the photoelectric switch 120B does not detect the electronic components C at the minimum approaching distance. Therefore according to this embodiment, the heights by which the X-ray irradiation unit 160 is restricted can be appropriately classified into the maximum approaching distance, the intermediate approaching distance, and the minimum approaching distance, depending on the detection results by the photoelectric switch 120A and the photoelectric switch 120B. As a result, unnecessarily strict restriction for the close-up function of the imaging device can be avoided. In the illustrated embodiment, the intermediate approaching distance has one dimension, but the present invention is not limited to the above mentioned embodiment. A plurality of photoelectric switches may constitute the intermediate sensor, and a plurality of intermediate approaching distances may be set.

In this embodiment, the inspection machine further provided with the board table 60 that holds the printed circuit board W, and the X axis driving mechanism 110 that drives the board table 60 relative to the X-ray camera unit 40 and the X-ray irradiation unit 160 as the imaging device along the surface of the printed circuit board W held by the board table 60. The X axis driving mechanism 110 moves the board table 60 as the driving means, whereby the X axis driving mechanism 110 serves functions as the displacement means, and relatively displaces the sensor unit 120 and the printed circuit board W. In other words, the X axis driving mechanism 110 can also play a role of the displacement means. Therefore according to this embodiment, the X-ray camera unit 40 and the X-ray irradiation unit 160 as the imaging device can irradiate the X-ray from various elevation angles. Hence, when the X axis driving mechanism 110 relatively drives the board table 60 and the imaging device, which is in the form of the X-ray camera unit 40 and the X-ray irradiation unit 160, diagonal images of the inspection target portion of the printed circuit board W held by the board table 60 can be taken. The X axis driving mechanism 110 serves functions as the displacement means, and relatively displaces the sensor unit 120 and the printed circuit board W, so that the printed circuit board W can be scanned utilizing the relative movement of the board table 60 and the X-ray camera unit 40 and the X-ray irradiation unit 160 as the imaging device before imaging is executed.

According to this embodiment, the movable frame 111 is disposed under the board table 60. A pair of X axis rails 112 and 113 that guide the board table 60 along the X axis direction is disposed on the movable frame 111. The X axis rails 112 and 113 as guide means that connects with the board table 60 so that the board table 60 can be relatively displaced along the X axis direction (the second direction in first embodiment) along the surface of the printed circuit board W supported by the board table 60. The sensor unit 120 is the reflection type photoelectric switches 120A and 120B which are installed in the movable frame 111 and in which the light emitting portion and the light receiving portion are assembled integrally, and the mirror 125, which reflects irradiation lights L1 and L2 irradiated from the light emitting portion 122 to the light receiving portion 123 in all the strokes where the board table 60 and the movable frame 111 are relatively displaced, is installed in the board table 60 at a position facing the sensor unit 120 via the printed circuit board W held by the board table 60. According to this embodiment, the surface of the printed circuit board W can be scanned by the reflection type photoelectric switches 120A and 120B installed on the movable frame 111 and the mirror 125 installed on the board table 60 in a compact layout.

According to this embodiment, the X axis driving mechanism 110 moves the board table 60 to the opening 11d (or opening 11e) of the printed circuit board W linearly along the second direction when the printed circuit board W is loaded, and the detection means irradiates the irradiation light in the first direction when the board table 60 loads the printed circuit board W from the opening 11d (or opening 11e). Therefore according to this embodiment, the heights of the electronic components C can be detected utilizing the movement when the printed circuit board W is loaded, and as a result, the X-ray camera 50 and the X-ray irradiation unit 160 can quickly execute the imaging processing for the printed circuit board W after the printed circuit board W is loaded.

According to this embodiment, the imaging device has the X-ray irradiation unit 160 that is disposed so as to be capable of approaching and separating from the printed circuit board W, and an X-ray camera 50 that receives an X-ray transmitted through the printed circuit board W from the X-ray irradiation unit 160. Therefore according to this embodiment, a required close-up image can be captured by making the X-ray irradiation unit approach the printed circuit board W.

The above described embodiment is merely a preferred example of the present invention, and the present invention is not limited to the above embodiment.

Now second embodiment will be described as shown in FIG. 13 to FIG. 21 as another embodiment of the present invention. In the following description, a composing element the same as first embodiment shown in FIG. 1 to FIG. 12 is denoted with a same reference symbol, for which redundant description is omitted.

Figure 13:
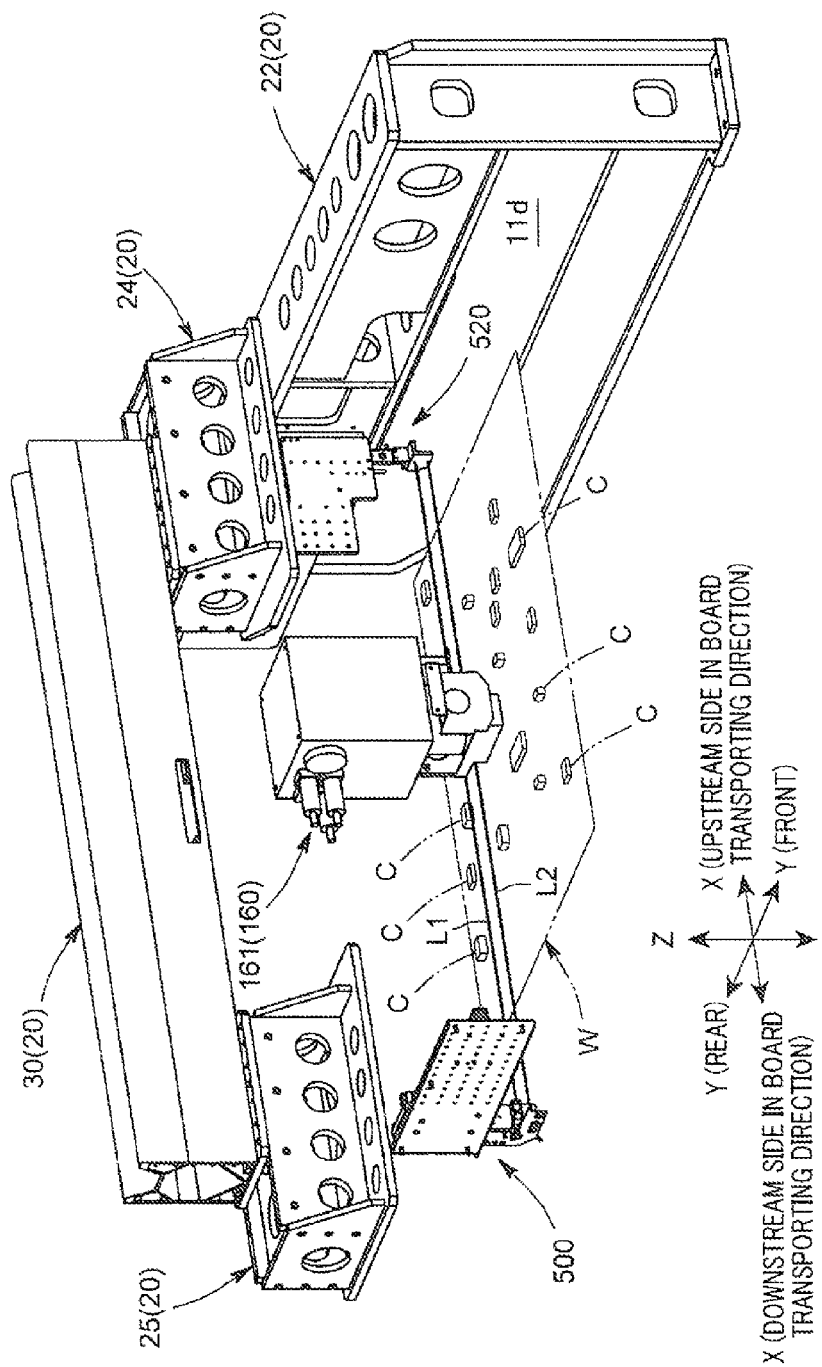
FIG. 13 is a perspective view depicting a key portion of an inspection machine according to second embodiment, which is another embodiment of the present invention.
Figure 14:
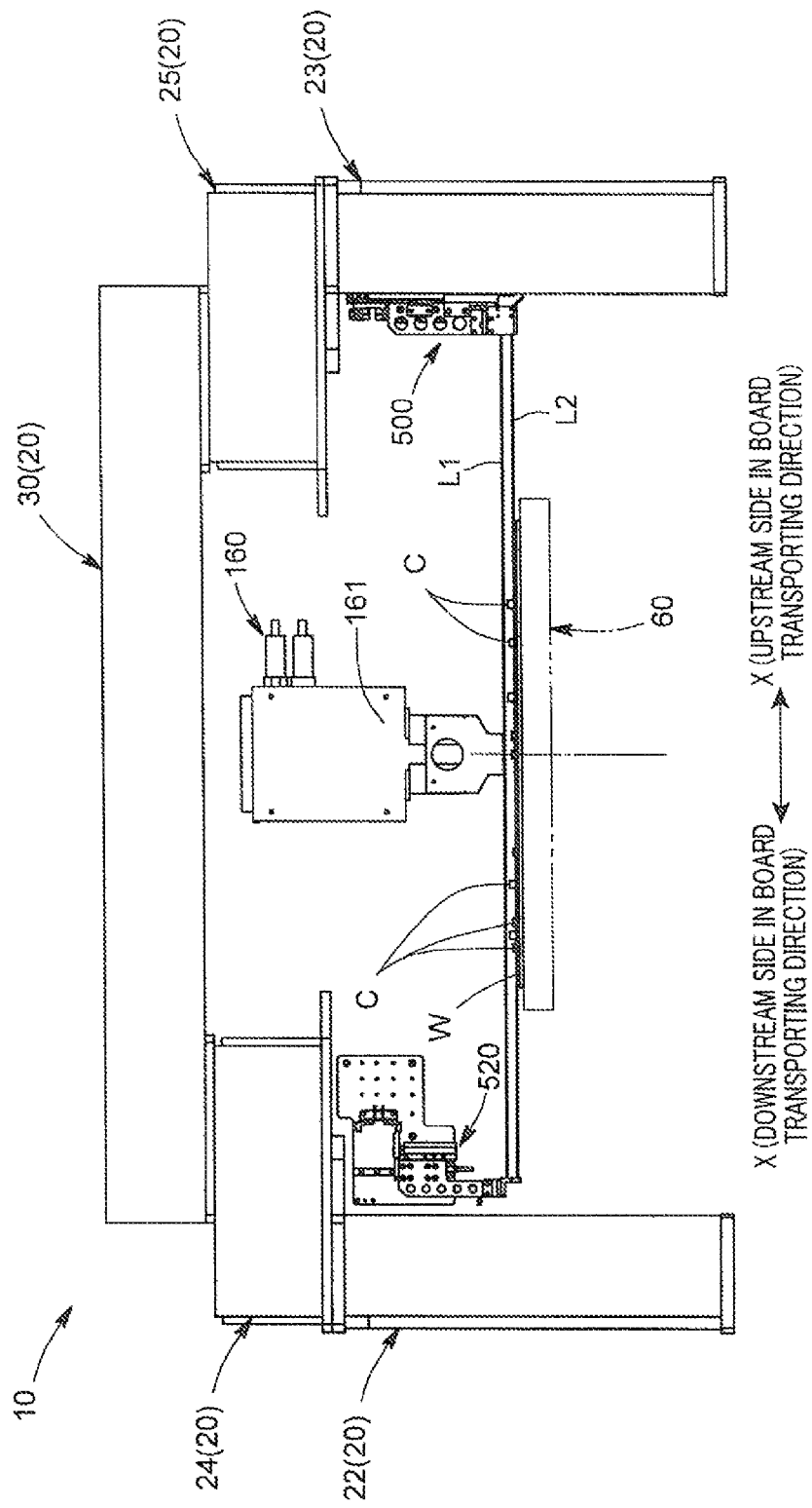
FIG. 14 is a partial schematic rear view depicting an overview of the inspection machine according to second embodiment.

As shown in FIGS. 13 and 14, a sensor unit 500 according to second embodiment is suspended from the bottom face of the frame unit 25 at the downstream side in the board transporting direction. A mirror unit 520 that operates in cooperation with the sensor unit 500 is suspended from the bottom face of the frame unit 24 at the upstream side in the board transporting direction. When the board table 60 is in a position facing the openings 11d and 11e of the housing 11 in the X axis direction, the sensor unit 500 and the mirror unit 520 face each other in a position shifted forward from the board table 60 along the X axis direction. As mentioned later, in the component height determination processing, the sensor unit 500 of second embodiment irradiates the irradiation light 500 along the X axis direction. Therefore in second embodiment, the X axis direction is the "first direction" of the present invention. The positions where the sensor unit 500 and the mirror unit 520 are installed are outside the loading or unloading path of the printed circuit board W, but are in a space where the printed circuit board W moves in plan view.

Figure 15:
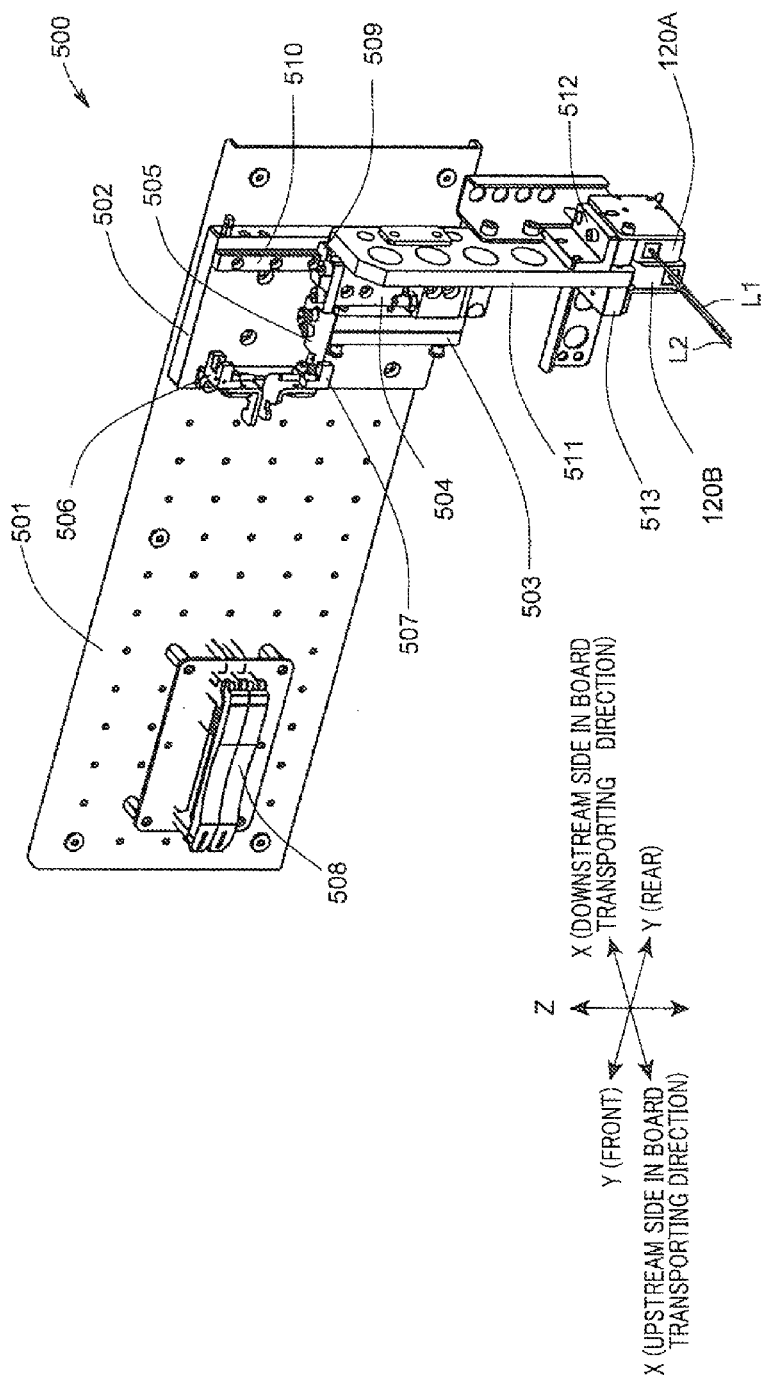
FIG. 15 is a perspective view of a sensor unit according to second embodiment.

As shown in FIGS. 15 and 16, the sensor unit 500 has a mounting plate 501 which is suspended from the bottom face of the frame unit 25, a base plate 502 secured to the mounting plate 501, an air cylinder 503 secured to the base plate 502, an elevation unit 504 which is vertically driven by the air cylinder 503, a dog 505 which is secured to the top end of the elevation unit 504, an upper switch 506 which detects the upper limit height of the dog 505, a lower switch 507 which detects the lower limit height of the dog 505, a connector 508 which connects a harness (not illustrated), a slider 509 which is secured to the side of the elevation unit 504, a guide rail 510 which is linked with the slider 509 so as to vertically guide the slider 509 and is secured to the base plate 502, and a bracket 511 which is mounted to the rear face of the elevation unit 504. The photoelectric switches 120A and 120B as the sensor unit 120 are secured to the bottom of the bracket 511 via mounting metal fittings 512 and 513.

The mounting plate 501 is a rectangular plate and is mounted to the bottom face of the frame unit 25 via a metal fitting (not illustrated). In this mounting state, the long side of the mounting plate 501 extends in the front to back direction. The mounting plate 501 has many mounting holes formed in a matrix, so that a required component can be mounted using any mounting holes. The base plate 502 is a metal member which is screwed into the rear portion of the mounting plate 501. The air cylinder 503 is secured to the base plate 502 in a state of the rod positioned vertically. The elevation unit 504 disposed on the rear side of the air cylinder 503 is linked to the rod. The elevation unit 504 ascends/descends on the rear face side of the air cylinder 503 by the rod of the air cylinder 503. The dog 505 is integrated with the upper end portion of the elevation unit 504 in an approximate horizontal state. The front end portion of the dog 505 protrudes forward from the air cylinder 503. The upper switch 506 and the lower switch 507 are disposed at the top and bottom, both facing the upper end portion of the dog 505. The upper switch 506 and the lower switch 507 are connected to the sensor system board 606 of the control unit 600 via the harness (not illustrated) so that signals can be outputted to the main control unit 601 of the control unit 600. The control unit 600 is configured to control the air cylinder 503 based on the output of the upper switch 506 and the lower switch 507. The connector 508 is secured in the front portion of the mounting plate 501. The harness connected to the connector 508 includes signal lines connected to the photoelectric switches 120A and 120B. The outputs of the photoelectric switches 120A and 120B are connected to the sensor system board 606 of the control unit 600 via the harness and the connector 508, so that signals can be outputted to the main control unit 601 of the control unit 600.

Figure 17B:
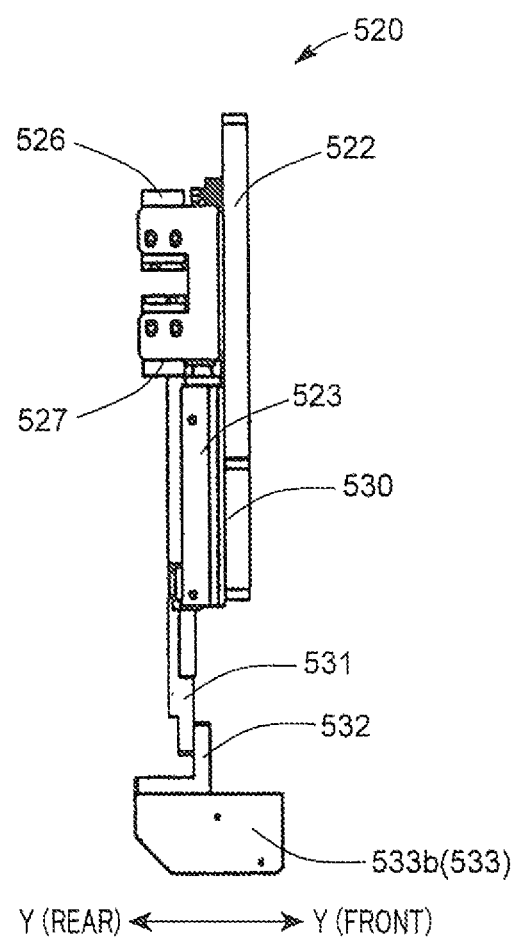
FIG. 17B is a schematic side view depicting an appearance of the mirror unit according to second embodiment.
Figure 19:
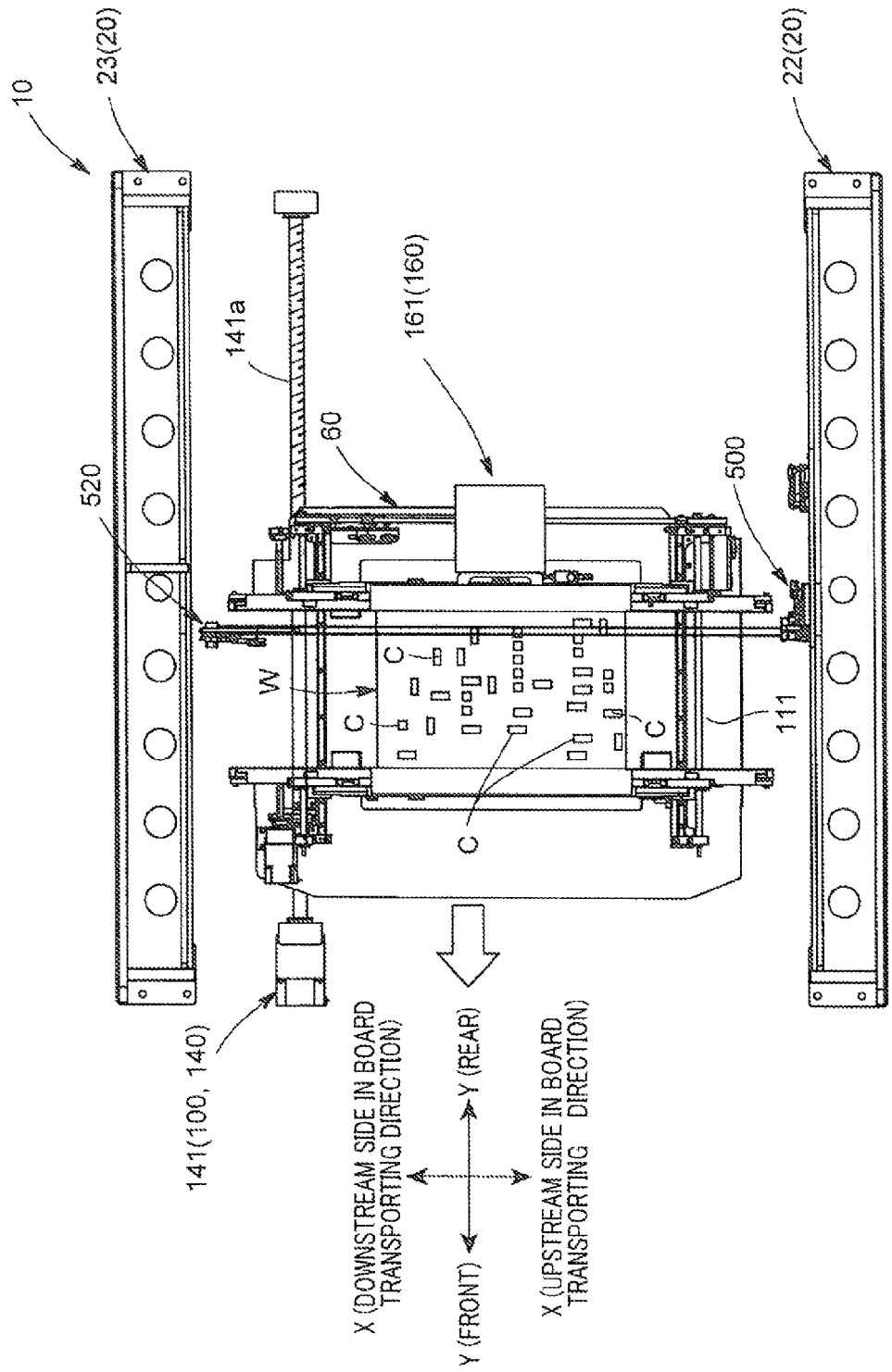
FIG. 19 is a schematic plan view depicting the inspection machine of second embodiment, where a part of the inspection machine is omitted.

As shown in FIGS. 17A and 17B, the mirror unit 520 has a base plate 522 which is suspended from the bottom face of the frame unit 24, an air cylinder 523 secured to the base plate 522, an elevation unit 524 which is vertically driven by the air cylinder 523, a dog 525 which is secured to the top end of the elevation unit 524, an upper switch 526 which detects the upper limit height of the dog 525, a lower switch 527 which detects the lower limit height of the dog 525, a slider 529 which is secured to the side of the elevation unit 524, a guide rail 530 which is linked with the slider 529 so as to vertically guide the slider 529 and is secured to the base plate 522, and a bracket 531 which is mounted to the rear face of the elevation unit 524. A reflection member 533 is secured to the bottom portion of the bracket 531 via the mounting metal fitting 532.

The base plate 522 is mounted to the bottom face of the frame unit 24 via a metal fitting (not illustrated). The base plate 522 is a plate member of which long side extends in the board transporting direction (X axis direction) at mounting. Many mounting holes are formed in a matrix in a portion of the base plate 522 at the downstream side in the board transporting direction, so that a required component can be mounted using any mounting hole. The air cylinder 523 is secured to the base plate 522 in a state of the rod positioned vertically. The elevation unit 524 disposed on the upstream side of the air cylinder 523 in the board transporting direction is linked to the rod. The elevation unit 524 ascends/descends on the upstream side of the air cylinder 523 in the board transporting direction by the rod of the air cylinder 523. The dog 525 is integrated with the upper end portion of the elevation unit 524 in an approximate horizontal state. The front end portion of the dog 525 protrudes to the downstream side in the board transporting direction, from the air cylinder 523. The upper switch 526 and the lower switch 527 are disposed at the top and bottom, both facing the upper end portion of the dog 525. The upper switch 526 and the lower switch 527 are connected to the sensor system board 606 of the control unit 600 via the harness (not illustrated), so that signals can be outputted to the main control unit 601 of the control unit 600. The control unit 600 is configured to control the air cylinder 523 based on the output of the upper switch 526 and the lower switch 527. The control unit 600 synchronizes the air cylinder 503 of the sensor unit 500 with the air cylinder 523 of the mirror unit 520. Therefore each air cylinder 503 and 523 simultaneously moves the elevation units 504 and 524 up/down in the same direction based on the control of the control unit 600. The mounting metal fitting 532 of the bracket 531 has a base plate portion which extends to the front and back in the Y axis direction. The reflection member 533 has a connection portion 533a that connects to the bottom face of the base plate portion and a mirror portion 533b which is suspended from the edge of the connection portion 533a.

The mirror portion 533b is disposed, at assembly, in a position facing the photoelectric switches 120A and 120B of the sensor unit 500 along the X axis direction. Therefore as shown in FIG. 13, FIG. 14, FIG. 18 and FIG. 19, the irradiation light L1 or L2 from each photoelectric switch 120A and 120B of the sensor unit 500 is irradiated from the downstream side to the upstream side in the board transporting direction, and is reflected by the mirror portion 533b from the upstream side to the downstream side in the board transporting direction.

As described above, in the plan view, the sensor unit 500 and the mirror unit 520 are disposed in the space where the printed circuit board W moves during inspection. Therefore the sensor unit 500 and the mirror unit 520 have the air cylinders 503 and 523 respectively for moving the elevation units 504 and 524 up and down. If each air cylinder 503 and 523 moves the elevation unit 504 or 524 up by extending the rod, the sensor unit 120 or the reflection member 533 disposed in the elevation unit 504 or 524 respectively is positioned above the printed circuit board W held on the board table 60, and does not interfere with the printed circuit board W even if the board table 60 moves to any position. If each air cylinder 503 and 523 retracts the rod and moves the elevation unit 504 or 524 down, the sensor unit 120 and the reflection member 533 face the board transporting direction at a height that is set in advance, as shown in FIG. 14, so that the heights of the electronic components C on the printed circuit board W can be detected by the irradiation light L1 or L2. According to second embodiment, each air cylinder 503 and 523 moves the elevation unit 504 or 524 down, whereby the detection movement means is constructed for moving the detection means so as to be displaced between an inspection position (inspection height) where the printed circuit board W enters a space where the printed circuit board W moves during inspection, and the irradiation light is irradiated, and a removing position (removing height) where the printed circuit board W is removed from the space.

As shown in FIG. 20, the differences of second embodiment shown in FIG. 13 to FIG. 21 from first embodiment are that the detection means descending step (step S11) is executed between steps S2 and S3, and the detection means ascending step (step S12) is executed between steps S3 and S4. Furthermore, in the step of detecting the heights of the electronic components C of the printed circuit board W in step S3, the second direction to drive the board table 60 is in the Y direction, which is different from first embodiment. These differences will now be described.

As shown in FIGS. 13, 14, 18, and 19, the sensor unit 500 and the mirror unit 520 face each other along the board transporting direction (X axis direction), and face the printed circuit board W at approximately the same height as the board table 60. In order to prevent the sensor unit 500 and the mirror unit 520 from interfering with the board table 60 in second embodiment, the rods of the air cylinders 503 and 523 are extended up in the initial state, so that the elevation units 504 and 524 are moved into the upper area. Since the printed circuit board W is loaded (step S1) in this state, the printed circuit board W can be loaded into a predetermined position in the housing 11, without interfering with the sensor unit 500 and the mirror unit 520. When the clamping is completed by the board table 60 (YES in step S2), the control unit 600 retracts the rods of the air cylinders 503 and 523 downward, and moves the elevation units 504 and 524 (step S11) down. By this descending operation, the irradiation lights L1 and L2 of the sensor unit 500 are irradiated in the X axis direction, from positions above the surface of the printed circuit board W held by the board table 60.

In this state, the control unit 600 detects the height of the electronic components C of the printed circuit board W (step S3). At this time, the control unit 600 activates the Y axis ball screw mechanism 141, and moves the board table 60 forward via the movable frame 111. Thereby the board table 60 advances from the state in FIG. 18 to the state in FIG. 19. By this advancement, the photoelectric switches 120A and 120B of the sensor unit 500 scan the printed circuit board W for the entire length of the printed circuit board W in the width direction (Y axis direction). As a result, the heights of all the electronic components C mounted on the printed circuit board W can be detected.

After detecting the heights of the electronic components C, the control unit 600 extends the rods of the air cylinders 503 and 523, so that the elevation units 504 and 524 are moved into the upper positions (step S512). Then even if the board table 60 moves in any direction in the subsequent component inspection step (step S5), the board table 60 never interferes with the sensor unit 500 and the mirror unit 520.

According to second embodiment, the detection movement unit that moves the sensor unit 120 or the like by the air cylinders 503 and 523 is also included. Therefore when the surface of the printed circuit board W is scanned by the sensor unit 120 before inspecting the printed circuit board W in second embodiment, the irradiation lights L1 and L2 can be irradiated at the inspection position where the printed circuit board W enters the space where the printed circuit board moves during inspection. Therefore the heights of the electronic components C can be detected at a level closest to the height of the printed circuit board W. As a result, even for a printed circuit board W on which small electronic components C are mounted, the facing distance which allows the X-ray camera unit 40 and the X-ray irradiation unit 160 as the imaging device to approach the printed circuit board can be set as short as possible, and restrictions for the close-up function can be minimized. During the inspection of the printed circuit board W, on the other hand, the sensor unit 500 and the mirror unit 520 are moved from the space. Therefore the interference between the printed circuit board W and the sensor unit 500, or the interference between the printed circuit board W and the mirror unit 520 during inspection, can be surely prevented.

In the above embodiments, the X-ray camera 50 is disposed below the board table 60 and the X-ray irradiation unit 160 is disposed above the board table 60, but the X-ray camera 50 may be disposed above the board table 60 and the X-ray irradiation unit 160 may be disposed below the board table 60.

In this embodiment, the X-ray camera unit 40 and the X-ray irradiation unit 160 as the imaging device are used, but an optical camera may be used as the imaging device, instead of the X-ray camera unit 40 and the X-ray irradiation unit 160, or together with the X-ray camera unit 40 and the X-ray irradiation unit 160.

As an embodiment of the present invention, if the printed circuit board W is kept a the same height when the board table 60 loads the printed circuit board W and when the printed circuit board W is inspected by the imaging device, the sensor unit 120 may irradiate the irradiation lights L1 and L2 in a direction crossing the movement direction of the board table 60 when the board table 60 moves from the loading entrance (opening 11d). In this case, the heights of the electronic components C can be detected utilizing the movement when the printed circuit board W is loaded, therefore the X-ray camera unit 40 and the X-ray irradiation unit 160 as the imaging device can quickly execute the imaging processing for the printed circuit board W after the printed circuit board W is loaded.

As another aspect (third embodiment), the inspection machine may be configured such that a predetermined approaching distance is set in advance, and an alarm is output if the X-ray irradiation unit 160 is unallowable to approach this approaching distance.

In concrete terms, a predetermined approaching distance is input using the display panel 610 and the keyboard 620, and is stored (registered) in the storage device 602 in advance. In this case, the display panel 610, the keyboard 620 and the storage device 602 as the setting means adapted to set a predetermined approaching distance in advance. If the approaching distance is set, a part of the flow chart in FIG. 11 or FIG. 20 mentioned above is changed as in FIG. 21, and executed.

As shown in FIG. 21, after step S4 in FIG. 11 or FIG. 20 is executed, the control unit 600 determines whether the X-ray irradiation unit 160 is allowable to approach at the approaching distance stored in the storage device 602, based on the detection result of the sensor unit 120 (step S20). As shown in FIG. 12, the limit distance is determined to one of the minimum approaching distance, the intermediate approaching distance, and the maximum approaching distance in step S4. The control unit 600 then compares the limit distance which was set in the sub-routine in step S4 with the approaching distance stored in the storage device 602, and determines that approaching is possible if the limit distance is the approaching distance or less, or determines that approaching is not possible if the limit distance exceeds the approaching distance.

If it is determined that approaching is possible, the control unit 600 executes steps S5 and S6 in the same manner as the processing shown in FIG. 11 or FIG. 20. On the other hand, if it is determined that approaching is not possible in the determination in step S20, or if it is determined that the X-ray irradiation unit 160 is unallowable to approach at the approaching distance that is stored in the storage device 602, the control unit 600 activates the lamp 611, and issues an alarm (step S21). Then the control unit 600 interrupts the inspection and executes error processing based on the preset program (step S22). This error processing includes stopping the apparatus, displaying the determination result, and display a GUI for operation to prompt the user to continue processing. According to third embodiment, the processing ends after step S22 ends.

According to third embodiment, the inspection machine further includes setting means (e.g. display panel 610, keyboard 620, storage device 602) adapted for user to set a required approaching distance in advance, determination means (control unit 600) that determines whether the X-ray irradiation unit 160 is allowable to approach at the approaching distance based on the detection result by the sensor unit 120, and alarm means (lamp 611) for warning an alarm when the determination means determines that the imaging device is unallowable to approach at the approaching distance. Therefore according to third embodiment, the user can set an approaching distance corresponding to the required inspection standard of the board in advance. The control unit 600 determines whether the X-ray irradiation unit 160 is allowable to approach at the approaching distance based on the detection result by the sensor unit 120. If it is determined that the X-ray irradiation unit 160 is unallowable to approach at the approaching distance, the lamp 611 generates an alarm. Since the user of the inspection machine can recognize that the electronic components cannot be imaged with the approaching distance set by the user, the user can take countermeasures for the inspection items or the like.

Needless to say, various changes can be made within the scope of the Claims of the present invention.

This application is based on Japanese Patent Application Serial No. 2012-096814, filed in Japan Patent Office on Apr. 20, 2012, the contents of which are hereby incorporated by reference.

What is claimed is:

1. An inspection machine for a printed circuit board on which a plurality of electronic components is mounted, comprising:
    an imaging device having a function for capturing a close-up of an inspection target portion of the printed circuit board by approaching the printed circuit board;
    a detection unit that detects heights of electronic components on the printed circuit board to be subjected to inspections by irradiation light that is irradiated onto the printed circuit board in a first direction that is along a surface of the printed circuit board;
    a displacement unit that relatively displaces the detection unit and the printed circuit board along the surface of the printed circuit board in a second direction that crosses the first direction; and
    a control unit that controls the detection unit and the displacement unit,
    wherein:
    the control unit controls the detection unit to detect the heights of the electronic components mounted on the printed circuit board by activating the detection unit and the displacement unit before capturing the printed circuit board by the imaging device, the control unit sets a limit distance to a position higher than the highest electronic component among heights detected from the electronic components, thereby restricting a facing distance, by which the imaging device is approachable to the printed circuit board, to be the limit distance.

2. The inspection machine for a printed circuit board according to claim 1, further comprising:
    a storage unit adapted to store a minimum approaching distance that is preset as a facing distance by which the imaging device is approachable to the shortest electronic component among the electronic components mounted on the printed circuit board subjected to inspection, a maximum approaching distance that is preset as a facing distance by which the imaging device is approachable to the highest electronic component among the electronic components mounted on the printed circuit board subjected to inspection, and an intermediate approaching distance that is preset as a facing distance between the maximum approaching distance and the minimum approaching distance,
    wherein:
    the detection unit includes a bottom sensor that detects the heights of the electronic components at a height corresponding to the minimum approaching distance; and
    an intermediate sensor that detects the heights of the electronic components at a height corresponding to the intermediate approaching distance.

3. The inspection machine for a printed circuit board according to claim 2, wherein:
    the control unit sets the limit distance to the maximum approaching distance when the intermediate sensor detects the electronic components at the intermediate approaching distance;
    the control unit sets the limit distance to the intermediate approaching distance when the intermediate sensor does not detect the electronic components at the intermediate approaching distance and the bottom sensor detects the electronic components at the minimum approaching distance; and
    the control unit sets the limit distance to the minimum approaching distance when the bottom sensor does not detect the electronic components at the minimum approaching distance.

4. The inspection machine for a printed circuit board according to claim 1, further comprising a board table that holds the printed circuit board, wherein the driving unit serves functions as the displacement unit.

5. The inspection machine for a printed circuit board according to claim 4, further comprising:
    a frame that is disposed under the board table and supports the driving unit; and
    a guide feature that connects the board table to the frame so that the board table are relatively displacable with respect to the frame along the second direction,
    wherein:
    the detection unit is installed in the frame and is constituted by reflection type photoelectric switches in which a light emitting portion and a light receiving portion are assembled integrally; and
    a mirror, adapted to reflect irradiation light irradiated from the light emitting portion to the light receiving portion in all strokes where the board table and the frame are relatively displaced, is installed in the board table at a position facing the detection unit via the printed circuit board held by the board table.

6. The inspection machine for a printed circuit board according to claim 4, wherein:
    the driving unit moves the board table to a loading entrance of the printed circuit board linearly along the second direction when the printed circuit board is loaded; and
    the detection unit irradiates the irradiation light in the first direction when the board table loads the printed circuit board from the loading entrance.

7. The inspection machine for a printed circuit board according to claim 1, further comprising a detection movement means adapted to move the detection unit between an inspection position where the irradiation light is irradiated in a space where the printed circuit board is moved for inspection, and a retracted position where the printed circuit board is retracted from the space.

8. The inspection machine for a printed circuit board according to claim 1, wherein the imaging device has an X-ray irradiation unit that is disposed so as to be capable of approaching and separating from the printed circuit board, and an X-ray camera that receives an X-ray transmitted through the printed circuit board.

9. The inspection machine for a printed circuit board according to claim 1, wherein further comprising:
    a setting device adapted to set a required approaching distance in advance;
    a determination unit that determines whether the imaging device is allowable to approach at the approaching distance based on the result obtained by the detection unit; and
    an alarm unit for warning an alarm when the determination unit determines that the imaging device is unallowable to approach at the approaching distance.

* * * * *